(12) United States Patent
Nisper et al.

(10) Patent No.: US 8,345,252 B2
(45) Date of Patent: Jan. 1, 2013

(54) METHOD AND SYSTEM FOR ENHANCED FORMULATION AND VISUALIZATION RENDERING

(75) Inventors: Jon Kenneth Nisper, Grand Rapids, MI (US); Thomas M. Richardson, Ada, MI (US); Marc S. Ellens, Grand Rapids, MI (US); Changbo Huang, San Francisco, CA (US)

(73) Assignee: X-Rite, Inc., Grand Rapids, MI (US)

( * ) Notice: Subject to any disclaimer, the term of this patent is extended or adjusted under 35 U.S.C. 154(b) by 967 days.

(21) Appl. No.: 12/401,129

(22) Filed: Mar. 10, 2009

(65) Prior Publication Data

US 2009/0213120 A1 Aug. 27, 2009

Related U.S. Application Data

(63) Continuation-in-part of application No. 11/810,012, filed on Jun. 4, 2007, now Pat. No. 7,944,561, which is a continuation-in-part of application No. 11/410,451, filed on Apr. 25, 2006, now Pat. No. 7,940,396.

(60) Provisional application No. 60/674,602, filed on Apr. 25, 2005.

(51) Int. Cl.
*G01N 21/55* (2006.01)
*G01J 3/46* (2006.01)

(52) U.S. Cl. .................. 356/445; 356/402; 356/448

(58) Field of Classification Search .................. None
See application file for complete search history.

(56) References Cited

U.S. PATENT DOCUMENTS

| | | | |
|---|---|---|---|
| 4,479,718 | A | 10/1984 | Alman |
| 4,711,580 | A | 12/1987 | Venable |
| 4,887,906 | A | 12/1989 | Koehler |

(Continued)

FOREIGN PATENT DOCUMENTS

DE 101 43 602 A1 4/2003

(Continued)

OTHER PUBLICATIONS

Baxter, et al., *A viscous paint model for Interactive Applications*, University of North Carlolina at Chapel Hill, 2004, available at http://gamma.cs.unc.edu./VISCOUS/.

(Continued)

*Primary Examiner* — Gordon Stock, Jr.
(74) *Attorney, Agent, or Firm* — McCarter & English, LLP

(57) ABSTRACT

An apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

A method of calculating xDNA, the vector sum of the observed reflectance intensity over a plurality of wavelengths and angles. Methods of using the calculated xDNA for formulating recipes for a surfaces colors. Furthermore, a method for using the calculated xDNA for rendering the surface color.

9 Claims, 22 Drawing Sheets

U.S. PATENT DOCUMENTS

| | | | |
|---|---|---|---|
| 5,137,364 | A | 8/1992 | McCarthy |
| 5,231,472 | A | 7/1993 | Marcus et al. |
| 5,241,369 | A | 8/1993 | McNeil et al. |
| 5,313,542 | A | 5/1994 | Castonguay |
| 5,583,642 | A | 12/1996 | Nakazono |
| 5,640,246 | A | 6/1997 | Castonguay et al. |
| 5,740,079 | A | 4/1998 | Shigemori et al. |
| 6,018,396 | A | 1/2000 | Rapaport et al. |
| 6,362,885 | B1 | 3/2002 | Osumi et al. |
| 6,373,573 | B1 | 4/2002 | Jung et al. |
| 6,414,756 | B1* | 7/2002 | Tsukada ............... 358/1.9 |
| 6,539,325 | B1 | 3/2003 | Numata et al. |
| 6,557,397 | B2 | 5/2003 | Langsch |
| 6,577,397 | B1 | 6/2003 | Wadman |
| 6,654,150 | B1* | 11/2003 | Rozzi ............... 358/520 |
| 6,707,553 | B1 | 3/2004 | Imura |
| 6,772,151 | B1 | 8/2004 | Johnston et al. |
| 6,952,494 | B2* | 10/2005 | Odagiri et al. ........ 382/162 |
| 6,963,426 | B2* | 11/2005 | Odagiri et al. ........ 358/1.9 |
| 7,046,375 | B2 | 5/2006 | Bischoff et al. |
| 7,064,830 | B2 | 6/2006 | Giorgianni et al. |
| 7,130,033 | B2 | 10/2006 | Delacour |
| 7,154,505 | B2 | 12/2006 | Coulthard |
| 7,259,852 | B2 | 8/2007 | Masuda |
| 7,277,174 | B2 | 10/2007 | Yamanouchi et al. |
| 7,466,415 | B2 | 12/2008 | Gibson et al. |
| 2001/0036309 | A1 | 11/2001 | Hirayama et al. |
| 2002/0097400 | A1 | 7/2002 | Jung et al. |
| 2002/0163640 | A1 | 11/2002 | Masuda |
| 2002/0165684 | A1* | 11/2002 | Olson ............... 702/85 |
| 2002/0167669 | A1 | 11/2002 | Schwarz |
| 2003/0179197 | A1* | 9/2003 | Sloan et al. ........ 345/426 |
| 2003/0234786 | A1* | 12/2003 | Cole et al. ........ 345/426 |
| 2004/0051874 | A1 | 3/2004 | Kubitzek |
| 2004/0150643 | A1* | 8/2004 | Borshukov ........ 345/426 |
| 2004/0218182 | A1 | 11/2004 | Alman et al. |
| 2004/0239919 | A1 | 12/2004 | Schwarz |
| 2005/0018191 | A1* | 1/2005 | Luo et al. ........ 356/404 |
| 2005/0018195 | A1 | 1/2005 | Lex |
| 2006/0023202 | A1 | 2/2006 | Delacour |
| 2006/0227137 | A1 | 10/2006 | Weyrich et al. |
| 2007/0291993 | A1* | 12/2007 | Nisper et al. ........ 382/108 |
| 2008/0170795 | A1* | 7/2008 | Akenine-Moller et al. .. 382/238 |
| 2008/0291449 | A1 | 11/2008 | Rodrigues et al. |
| 2009/0141976 | A1* | 6/2009 | Tsukada ........ 382/167 |
| 2009/0213120 | A1* | 8/2009 | Nisper et al. ........ 345/426 |
| 2010/0020081 | A1* | 1/2010 | Tsuboi et al. ........ 345/440 |
| 2010/0328740 | A1* | 12/2010 | Tsukada ............... 358/530 |
| 2011/0191067 | A1* | 8/2011 | Robles-Kelly et al. ....... 702/189 |

FOREIGN PATENT DOCUMENTS

| | | |
|---|---|---|
| EP | 1 217 346 | 6/2002 |
| FR | 2 860 869 A1 | 10/2003 |
| WO | WO 2005/072448 A2 | 8/2005 |
| WO | WO 2008/063606 A2 | 5/2008 |
| WO | WO 2008/121358 A1 | 10/2008 |

OTHER PUBLICATIONS

Baxter, et al., *A viscous paint model for Interactive Applications*, Computer Animation and Virtual Worlds Journal, Jul. 2004.

William V. Baxter, Jeremy Wendt, and Ming C. Lin, "IMPaSTo: A realistic, interactive model for paint." In Stephen N. Spencer (ed.), *Proceedings of the 3rd International Symposium on Non-Photorealistic Animation and Rendering*, Annecy, France, Jun. 5-7, 2004.

Caivano, Jose Luis, *Cesia: A system of Visual Signs Complementing Color*, Color research and application 16(4), Aug. 1991.

Caivano, Jose Luis, *The Representation of the Visual World in Photography*, Society for Imaging Science and Technology, 2008, p. 189-193.

Ershov, et al., *Reverse Engineering approach to appearance-based design of metallic and pearlescent paints*, The Visual Computer, Oct. 12, 2004.

William Baxter and Ming Lin, *A Versatile Interactive 3D Brush Model*, Proc. of Pacific Graphics, Oct. 2004, available at http://gamma.cs.unc.edu/BRUSH/.

William V. Baxter, Vincent Scheib, Ming C. Lin, and Dinesh Manocha "DAB: Interactive Haptic Painting with 3D Virtual Brushes." In Eugene Fiume (ed.), *Proceedings of the 28th Annual Conference on Computer Graphics and Interactive Techniques, SIGGRAPH 2001*, Los Angeles, CA, Aug. 12-17, 2001, pp. 461-468. Available at http://gamma.cs.unc.edu/DAB/.

Curtis, et al., "Computer Generated Watercolor." In *SIGGRAPH 2001*, Los Angeles, CA, Aug. 3-8, 1997, pp. 461-468. Available at http://grail.cs.washington.edu/projects/watercolor/.

Nelson S.-H. Chu and C.-L. Tai, Real-time Painting with an Expressive Virtual Chinese Brush. *IEEE Computer Graphics and Applications*, Sep./Oct. 2004 (vol. 24, No. 5). pp. 76-85.

Nelson S.-H. Chu and C.-L. Tai, An Efficient Brush Model for Physically-Based 3D Painting, *Proc. of Pacific Graphics 2002*, Oct. 9-11, Beijing, China, IEEE Press.

Jeng-Sheng Yeh, Ting-Yu Lien, Ming Ouhyoung, "On the Effects of Haptic Display in Brush and Ink Simulation for Chinese Painting and Calligraphy", Proc. of Pacific Graphics 2002 (PG2002), pp. 439-441, Oct. 2002, Beijing, China, IEEE Press.

http://www.refractometer.com/abberefrac.html (last visited on Mar. 26, 2010)—Link not working.

http://www.microphotonics.com/se500.html (as of Mar. 13, 2006 using wayback machine).

http://www.datacolor.com/uploads/broch_multifx10_en.pdf (as of Mar. 13, 2006 using wayback machine).

X-Rite, The Color Guide and Glossary, Communication, measurement, and control for Digital Imaging and Graphic Arts, 2004.

BBC News, *Laser spots paper 'fingerprints'*, available at http://news.bbc.co.uk/2/hi/technology/4741809.stm, Aug. 3, 2005.

PCT International Search Report (PCT/US2006/015600 filed Sep. 14, 2006).

Ershov, et al., Rendering Pearlescent Appearance Based on Paint-Composition Modeling, Eurographics, 2001, vol. 20 No. 3.

Harvey, Light Scattering Properties of Optical Surfaces, Dissertation, University of Arizona, 1976.

Standard Practice of Angle Resolved Optical Scatter Measurements on Specular or Diffuse Surfaces, ASTM International; Designation: E 2387-05, (no date).

European Extended Search Report for EP 2,228,634 dated Jul. 2, 2010.

* cited by examiner

800

```
┌─────────────────────────────┐
│   Find First Moment         │
│                      802    │
└─────────────────────────────┘
              │
              ▼
┌─────────────────────────────┐
│   Find Mean Spectral        │
│   First Moment              │
│                      804    │
└─────────────────────────────┘
              │
              ▼
┌─────────────────────────────┐
│  Find Weighted Spectral     │
│  Spatial Distribution  806  │
└─────────────────────────────┘
```

FIG. 8

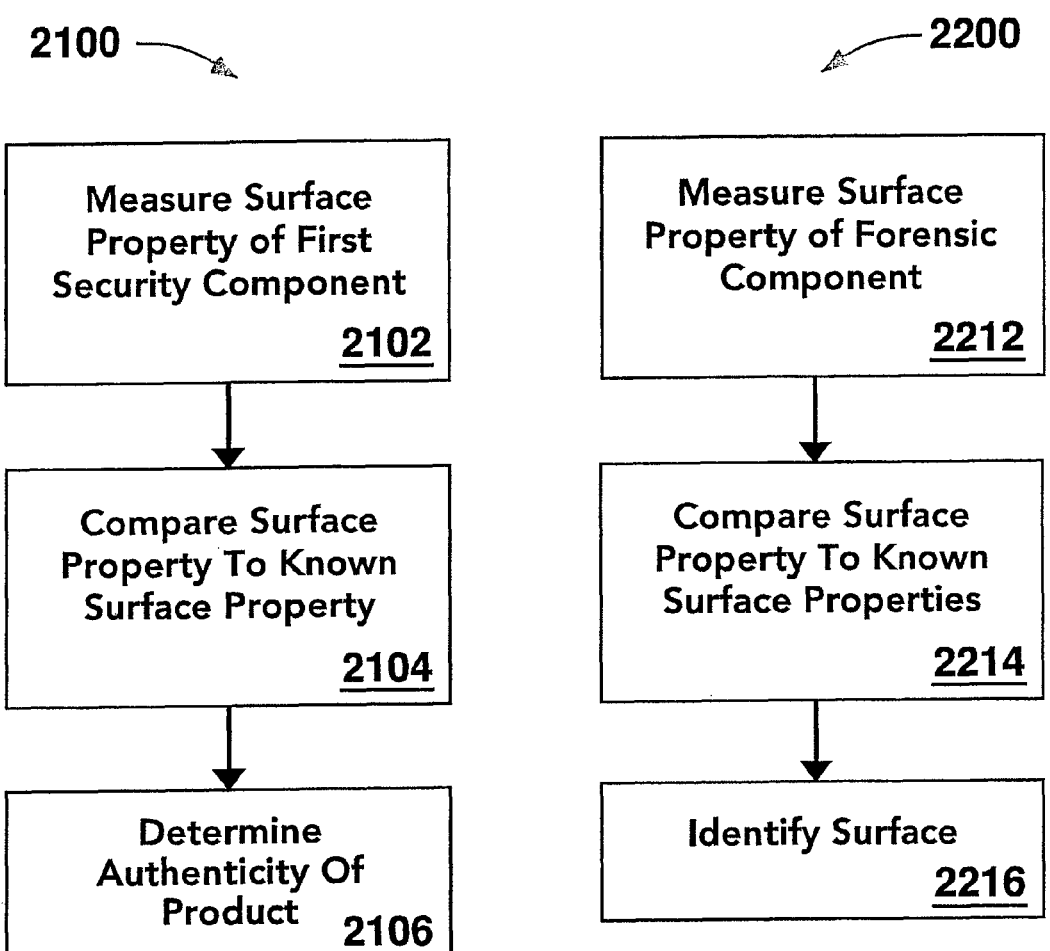

METHOD AND SYSTEM FOR ENHANCED FORMULATION AND VISUALIZATION RENDERING

CROSS-REFERENCE TO RELATED APPLICATION

This application claims the benefit of a co-pending non-provisional patent application entitled "Measuring an Appearance Property of a Surface Using a Bidirectional Reflectance Distribution Function," which was filed on Jun. 4, 2007 and assigned Ser. No. 11/810,012, which in turn claimed priority to U.S. patent application Ser. No. 11/410,451, filed on Apr. 25, 2006, which in turn claimed priority to U.S. Provisional Application No. 60/674,602, filed on Apr. 25, 2005. All of the foregoing applications are incorporated herein by reference.

BACKGROUND

Many methods and devices have been developed for measuring and describing the visual appearance of objects. These methods and devices are useful in a variety of contexts. For example, measurements of the visual appearance of an object can reveal properties of any paints, pigments, specialty coatings, surface treatments, etc., that may be present on the object. Also, for example, measurements of the visual appearance of an object can be used to create computer models, set production tolerances, etc. It is known to use various devices to provide spectral measurements of a surface of an object. Existing devices, however, either produce results of limited detail or are exorbitant in cost, size, and the time necessary for measurements.

For example, it is known to use discrete multi-angle spectrometers that measure reflectance over a limited number of viewing and illumination directions. An example of such a device is the MA68 available from X-RITE. All of these devices, however, either consider a limited number of viewing directions (e.g., coplanar directions), or consider data derived from all viewing angles together, for example, by summing or averaging over all directions. As a result, known discrete multi-angle spectrometers provide results that do not reflect directional variations in surface appearance. Referring to the coatings industry, these results can be useful to measure some properties of surfaces including conventional paints, pigments, and coatings. They are not as useful, however, for measuring properties of surfaces having specialized paints, pigments, and other specialty coatings that have different appearances when viewed from different angles, such as those that appear today on cars, boats, currency, consumer plastics, cosmetics, etc. For example, limited sample multi-angle spectrometers are not as useful for measuring properties of interference coatings such as, for example, pearlescent automotive paints that appear one color {e.g., white) from one angle and a second color (e.g., pink) from another angle. They also typically do not provide detailed enough results to tie properties of a surface back to physical features of the surface, for example, due to coating formulation and/or application process factors.

Some of the shortcomings of known discrete multi-angle spectrometers are addressed by devices that measure the complete Bidirectional Reflectance Distribution Function (BRDF) of a surface, such as goniospectrophotometers and parousiameters. The complete BRDF generated by these devices provides a rich characterization of the scatter off of a surface as a function of illumination angle, viewing angle, wavelength and other variables. Both of the referenced devices for measuring BRDF, however, have significant drawbacks.

Goniospectrophotometers, such as the GCMS-4 Gonio-Spectro-Photometric Colorimeter available from MURAKAMI, measure the complete BRDF by scanning both illumination and detection angles, typically over a complete hemisphere. Although they can provide good results, the devices are extremely large and expensive. Also, it can take several hours to scan illumination and detection angles over a complete hemisphere, making real-time applications impossible. Parousiameters, such as the one described in U.S. Pat. No. 6,557,397 to Wademan, measure the complete BRDF by projecting a range of illumination and detection angles onto a hemispheric screen and imaging the screen using a camera. The error of these devices, however, is directly related to the size of the hemispherical screen, and the devices cannot acceptably measure samples with an area greater than 10% of their screen's area. As a result, parousiameters are often large and bulky. Also, slots in the screen, and the limited dynamic range of most high resolution cameras further limit the device. In addition, because both goniospectrophotometers and parousiameters measure illumination and viewing angles over a complete hemisphere, noise issues can become a significant factor.

Spectrophotometers are used for the measurement of objects to provide spectral reflectance data that is converted into tristimulus colorimetric results, which may then be used for communication and display. This data is also used in developing ink formulations, pigments, and dyes used in the coloring of products meant to replicate the appearance of a measured object. In many cases, other features of the objects to be measured complicate the measurement process, making it difficult to obtain repeatable results. The dimensions of Cesia and Spatiality may be used to describe these additional perceptual effects (the physical equivalent dimensions of periodic and aperiodic subsurface scatter, spatial roughness, and local slope variation). Texture, coarseness and sparkle are examples of types of Cesia and Spatiality that can alter the perceived color of an object under different types of illumination and are of interest in recreating and replicating an image/object, e.g., when simulating appearance on a computer screen and/or when developing a recipe or formulation for replicating an object's color or appearance.

Traditional methods of formulation and rendering do not accurately account for the noted effects and often simply ignore them. The net result is an inaccurate estimation of the true color of the object along with a failure to account for these effects. A simple example is a metallic automotive paint, where the addition of metal flakes provides a "sparkling" effect under directional illumination, and the perception of dimensional "coarseness" when viewed under diffuse illumination. Without the metallic flakes, the base diffuse color would appear darker. Addition of metallic flakes tends to lighten the apparent color of the object while simultaneously providing a sparkling effect. Additionally, process effects may cause the perceived lightening to change based on viewing and illumination angle. Furthermore, variations in flake size distribution may cause batch-to-batch variations that are perceptible, e.g., as color and/or sparkle differences, even though the nominal flake size remains constant.

Historically, spectrophotometers used to measure object color have typically involved a single illuminator and a single receiver configured in a 0/45 or 45/0 configuration (illumination angle/receiver angle relative to surface normal). However, due to the other perceptual dimensions of Cesia and Spatiality (physical equivalent dimensions of periodic and aperiodic subsurface scatter, spatial roughness and local slope variation), such instrumentation is unable to provide repeatable results for most common objects, particularly when such objects are rotated and/or moved about. Furthermore, renderings and formulations based on measurements made with conventional spectrophotometer instruments will yield inaccurate results except for the simplest of cases.

For most situations, the historical solution has involved either providing diffuse illumination or diffuse receiver (or both) by changing the optics or through the addition of an integrating sphere. However, sphere-based spectrophotometers tend to simply "average up" the results, integrating the goniometric and spatially-distributed changing color and lightness reflectance over a hemisphere so as to provide a single result. While this functionality helps to remove rotation- and translation-based measurement instability, it results in a single spectral curve that combines the Cesia and Spatiality effects with the color, resulting in an incorrect color result.

Multi-angle and scanning goniospectrophotometers overcome the foregoing limitations by providing multiple angles of illumination and receiving pickup. As a result, many spectral curves are generated that characterize the response of the sample under each illumination and observation (receiving) condition. Examples of such instruments include the Revolution system available from IsoColor Inc. (Carlstadt, N.J.), the SOC200 available from Surface Optics Corp (San Diego, Calif.), the BYK-MAC available from BYK-Gardner (Columbia, Md.), and the MA98 available from X-Rite, Inc. (Grand Rapids, Mich.). A challenge presented by these commercially available instruments is that they are able to generate a large number of spectral curve results in a very short time with only a few measurements. Even if the data is reduced to 3 dimensional color space results, there are still many different answers for a single measurement object, raising the question: Which result (illumination/observation angle) is the "single correct" color? Indeed, each result correctly represents the color of the object for a given set of illumination/observation conditions. In view of the above-noted challenge, current commercial instrumentations are not equipped to efficiently and effectively use spectral curve data, e.g., to provide an accurate rendering visualization on a computer screen and/or to develop a formulaic recipe.

Computer visualization shares many similarities to the development of a formulaic recipe for color replication. Both situations seek to simulate the response of light as it impinges on an object of given composition to generate a desired color response. Examples abound in the computer graphics literature and technical literature. Most commonly, an object's response to light is defined by the BRDF mathematical function referenced above. Of note, the BRDF function may be referenced in various ways, e.g., BSSRDF and BTF, depending on the specific implementation of the measurement configuration. Generally, each of the noted regimens are aimed at capturing how an object's illumination is modified and transformed by the object to generate its reflectance (and transmittance) in different directions.

In the simple case of a 0/45 spectrophotometer or an integrating sphere spectrophotometer, the fact that only a single spectral curve is generated for a single measurement has been addressed, e.g., in the computer graphics industry, through simplified mathematical reflectance lobe functions commonly known as Phong, Blinn-Phong, Cook Torrance, La Fortune, etc. These models assume that the single color measurement result is fundamentally correct and modify this base color to create common Cesia effects such as Gloss. However, the information required for modification is not typically available from the measurement and other knowledge about the object is required to correctly model and visualize the higher order effects, e.g., spatiality, and to accurately model Cesia effects. Furthermore, if the original object is glossy or features texture(s), then the single spectral curve measurement results will contain the contribution of these effects and, therefore, modeling of even the basic diffuse color will be inaccurate.

In the case of formulation, the problems are similar. Assuming only a single spectral curve, formulation software optimization models use a database of material properties to combine contribution of effects to create estimates of spectral response. These predicted results are compared to the measured (or desired) results and the error minimized through the use of merit functions. Common models include Kabelka Munk, Multiflux Phase, Effective Medium Theory, and other similar derivatives. The noted models share a great deal of similarity to the computer visualization models and, therefore, suffer many of the same deleterious effects. More particularly, the noted models utilize simple concepts of additive and subtractive color (absorption and reflection) as well as gross assumptions regarding subsurface scattering, and simple weighting functions to predict the spectral response of the material (or coating). This prediction is compared against the measured or desired results and the error difference minimized through iteration. Because the models are simplified and the single spectral curve contains the same assumptions and errors described above due to the inclusion of Cesia and Spatiality effects, the results are prone to error. Corrections are made to the models to account for gross assumptions, such as Fresnel Reflectance Coefficients and their relationship to the dielectric constants, but errors due to process effects giving rise to Cesia and Spatiality (e.g., agglomeration and orange peel in automotive paints) are not accounted for.

Indeed, conventional software is formulaic in nature, creating only a recipe of ingredients and amounts—there is little or no attempt to account for batch or production process induced variation in the formulation process. However, such process effects typically modify the Cesia and Spatiality of the object and therefore directly and/or indirectly affect the color of the object both physically and in the net measurement result (thus further inducing error in the optimization process).

With the introduction of multiangle and scanning goniospectrophotometers, more robust rendering and formulation software has been developed. Models such as the Multi Flux Phase (with additional terms), the Henyey Greenstein formalization, and the Fuzzy Logic methods of Osumi et al., allow for additional terms to modify the shape of the BRDF lobe from spherical or elliptical to higher order shapes depending on the number of terms involved. These models improve on the simple single spectral curve and assumed mathematical BRDF lobe functions described above. Although such modifications accommodate the optimization utilizing many spectral curves (as opposed to one), they do not attempt to utilize the information contained in the desired set of spectral curves to decompose process effects from formulation effects and recipe changes. There is no attempt made to classify potential ingredients other than traditional "n" and "k" (dielectric constant and scatter coefficients). As a result, they still suffer from the same inability to separate process induced Cesia and Spatiality changes from formulaic batch variability and recipe changes.

Thus, despite efforts to date, a need remains for a method of measuring an object's true color accounting for physical material-related properties, such as Cesia and Spatiality, derived from both batch variability and recipe changes. A need also remains for visualization and formulation of true color that incorporates the effects of both batch variability and recipe changes on physical material related properties. These and other needs are satisfied by the systems and methods disclosed herein.

SUMMARY

In one general aspect, the present disclosure is directed to an apparatus for measuring a spatially under-sampled Bidirectional Reflectance Distribution Function (BRDF) of a surface. The apparatus may comprise a first light source directed to illuminate the surface from a first illumination direction, and a plurality of sensors positioned to receive light reflected by the surface. The plurality of sensors may comprise first, second and third sensors positioned to receive light reflected by the surface in first, second and third non-coplanar directions. In various embodiments, the apparatus may also comprise a computer in communication with the plurality of sensors. The computer is configured to convert light sensed by the plurality of sensors into a first appearance property of the surface considering the first, second, and third reflectance directions.

In another general aspect, the present disclosure is directed to methods for measuring a spatially under-sampled Bidirectional Reflectance Distribution Function (BRDF) of a surface. The methods comprise the steps of illuminating the surface with a first light source incident on the surface from a first illumination direction, and sensing light of a plurality of wavelengths reflected by the surface in a plurality of reflectance directions. The plurality of reflectance directions include a first reflectance direction, a second reflectance direction and a third reflectance direction. The methods also comprise the step of converting the light into a first appearance property of the surface considering the first, second, and third reflectance directions.

A further exemplary embodiment of the present disclosure provides systems and methods that are adapted to calculate the vector sum of the first reflectance direction, the second reflectance direction and the third reflectance direction over a plurality of wavelengths. The vector sums are then plotted on a three-dimensional surface to create a three dimensional curve to describe the color of the object. The foregoing three-dimensional curve is referred to herein as "xDNA". Accessing database(s) containing xDNA for known material(s), process(es) and/or batch characteristics, a formulation for a surface may be advantageously predicted. Through the use of merit functions, this formulation may be further refined to yield a more accurate formulation recipe or visualization model. The formulation may also be used to render the color of an object on visual display units, including computer graphic displays.

Thus, the present disclosure provides advantageous methods and systems for formulation, rendering and visualization. More particularly, xDNA value(s) may be calculated and used to extract properties related to formula, recipe and/or ingredient parameters. The xDNA value(s) may be used for direct formulation, to produce a better starting point, and/or as a merit function. Indeed, the xDNA value(s) take into account—and thereby facilitate the creation of formulations, renderings and visualizations that take into account—important variables, e.g., appearance properties that are influenced by physical material. Thus, xDNA value(s) may be used to directly address variables such as concentration, pigment grind (particle size), mean flake size, and the like. Further refinements can be achieved, e.g., using the steps of translate, rotate, align, to remove error and differences between measurements of a sample and of a calibration plate, thereby removing variability due to process, and focusing the formulation (or rendering model) on the basic recipe (or material mode) to derive (or drive) parameters that relate to or are identified as ingredients in the material.

Various other embodiments of the invention are directed to systems for measuring a spatially under-sampled Bidirectional Reflectance Distribution Function (BRDF) as well as practical applications. In various aspects, the invention is directed to methods of matching the appearance of coatings applied to two components, methods of repairing a device, and methods of finding the identity of an unknown object.

BRIEF DESCRIPTION OF THE FIGURES

Embodiments of the present invention are described herein, by way of example, in conjunction with the following figures, wherein:

FIG. 8 shows a flow chart illustrating a process flow according to various embodiments of the present invention;

FIGS. 17-22 show flow charts illustrating process flows according to various embodiments of the present invention;

DETAILED DESCRIPTION OF EXEMPLARY EMBODIMENTS

Embodiments of the present invention are directed to methods and apparatuses for measuring and/or analyzing a spatially under-sampled Bidirectional Reflectance Distribution Function (BRDF) of a surface. When light is incident on a surface, a portion of the light is reflected, scattered or otherwise directed away from the surface over various directions. The BRDF of a surface is an expression of the intensity of this reflectance over all or multiple wavelengths and reflectance directions as a function of illumination angle and other variables (e.g., polarization). According to various embodiments, the BRDF of a surface is spatially under-sampled by measuring the intensity of reflectance at only a discrete number of reflectance directions. In various embodiments, the discrete reflectance directions may be non-coplanar. The measured reflectance may then be processed to derive one or more appearance properties of the surface under observation. The appearance properties may reflect directional variation in the appearance of the surface, as captured by the measured reflectance.

Figure 1:
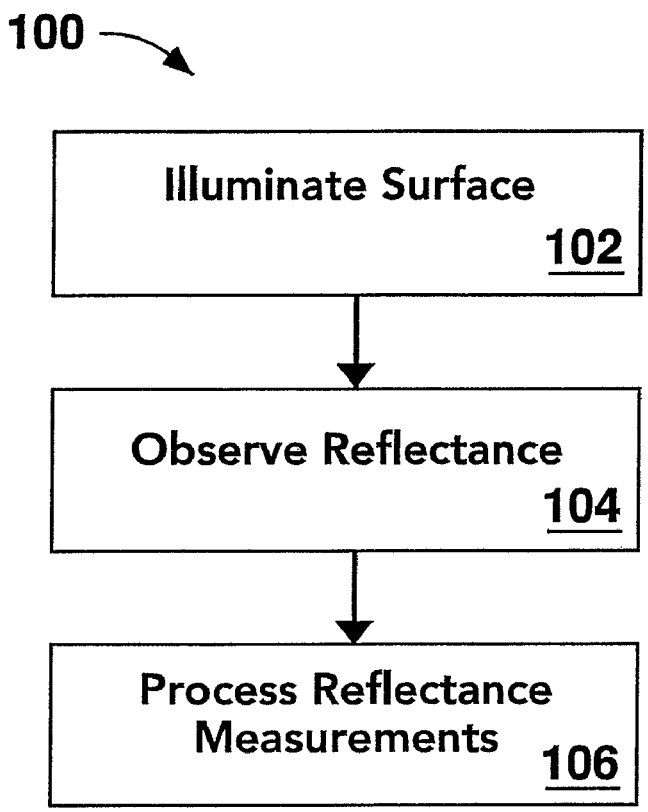
FIG. 1 shows a flow chart illustrating a process flow according to various embodiments of the present invention.

FIG. 1 shows a flow chart illustrating a process flow 100 for measuring and processing a spatially under-sampled BRDF of a surface according to various embodiments. At step 102, light may be directed toward the surface. The light may be formed into one or more beams, which may be collimated or non-collimated. The light may originate from one or more broad spectrum illumination sources and may be incident on the surface from one or more illumination directions. The number of illumination sources and illumination directions may vary based on the particular application. It will be appreciated, however, that increasing the number of illumination sources and/or directions may increase the quality of the resulting BRDF. It will be appreciated that, the illumination direction or directions may form any angle with the surface normal. In various embodiments, however, the illumination direction or directions may form angles with the surface normal of between zero and sixty-five degrees {e.g., zero degrees, 45 degrees, etc.).

At step 104, the intensity of the reflectance off of the surface in a plurality of discrete reflectance directions may be measured. It will be appreciated that these measured reflectances, along with the corresponding reflectance directions, represent a spatially under-sampled BRDF of the surface. In various embodiments, the complete set of reflectance directions may be non-coplanar. Also, in various embodiments, multiple measurements may be taken at each reflectance direction, with each measurement recording the reflectance intensity at a particular wavelength or wavelength range. In various embodiments, the measurements may be taken from fixed sensors, with one sensor fixed on each of the plurality discrete reflectance directions. It will be appreciated that because the reflectance is being measured only in discrete directions, and not in every direction, that the time necessary to measure the reflectance may be less than that taken by complete BRDF devices (e.g., goniospectrophotometers and parousiameters). In various embodiments, the measurements may be taken in under five seconds.

The spatially under-sampled BRDF may be expressed as a series of reflectance vectors representing the observed intensities at each reflectance direction. For example, each observed reflectance direction may have a vector pointing in the reflectance direction with a magnitude equal to the observed reflectance intensity in the reflectance direction. It will be appreciated that if multiple wavelengths or wavelength ranges are observed in a reflectance direction, then reflectance directions may have a vector corresponding to each of the wavelengths or wavelength ranges.

Figure 2:
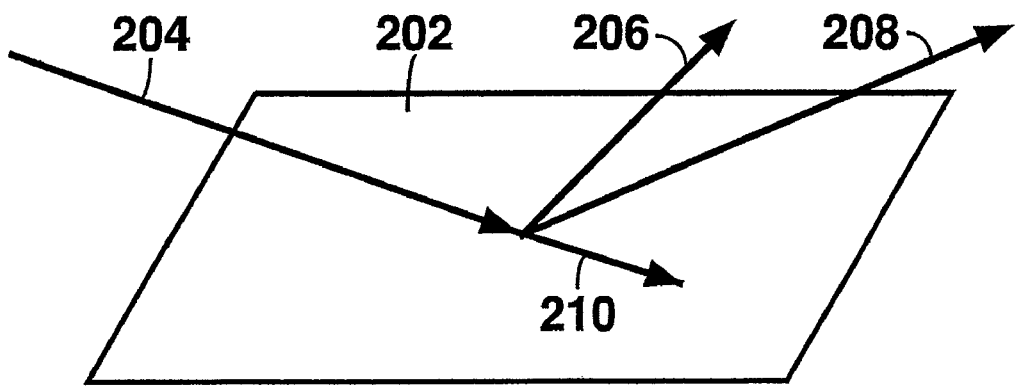
FIG. 2 shows a diagram of reflectance from a surface according to various embodiments of the present invention.
Figure 3:
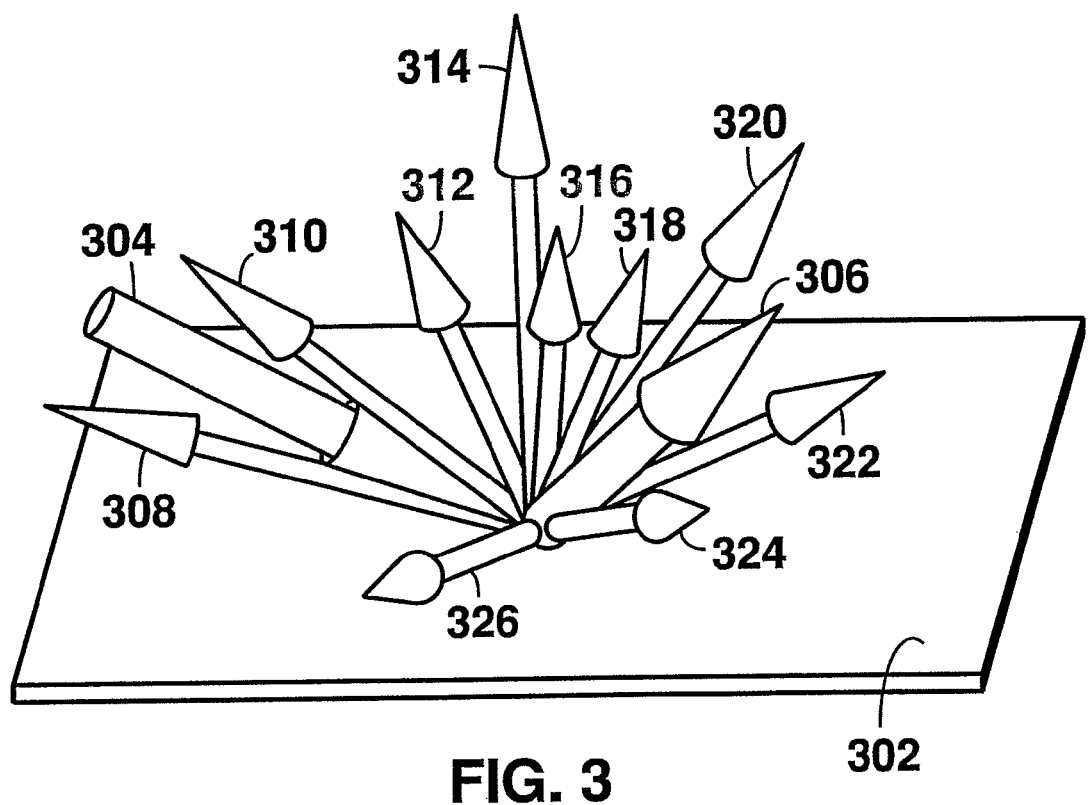
FIG. 3 shows a diagram of reflectance from a surface according to various embodiments of the present invention.

As an illustration, FIG. 2 shows an exemplary surface 202 with light incident on the surface 202 from an illumination direction 204. Three discrete non-coplanar reflectance directions 206, 208, 210 are observed. FIG. 3 shows another exemplary surface 302 according to various embodiments having incident light from one illumination direction 304 and eleven observed reflectance directions 306, 308, 310, 312, 314, 316, 318, 320, 322, 324 and 326. It will be appreciated that the number and identity of the reflectance directions may vary. For example, in various embodiments, there may be between five and fifteen reflectance directions. Also, in various embodiments, the reflectance directions may include industry standard reflectance directions (e.g., those having aspecular angles of 15, 25,45, 75 and 100 degrees.) Also, in various embodiments, at least one of the reflectance directions may be chosen orthogonal to the illumination direction relative to a surface normal of the surface.

Figure 4:
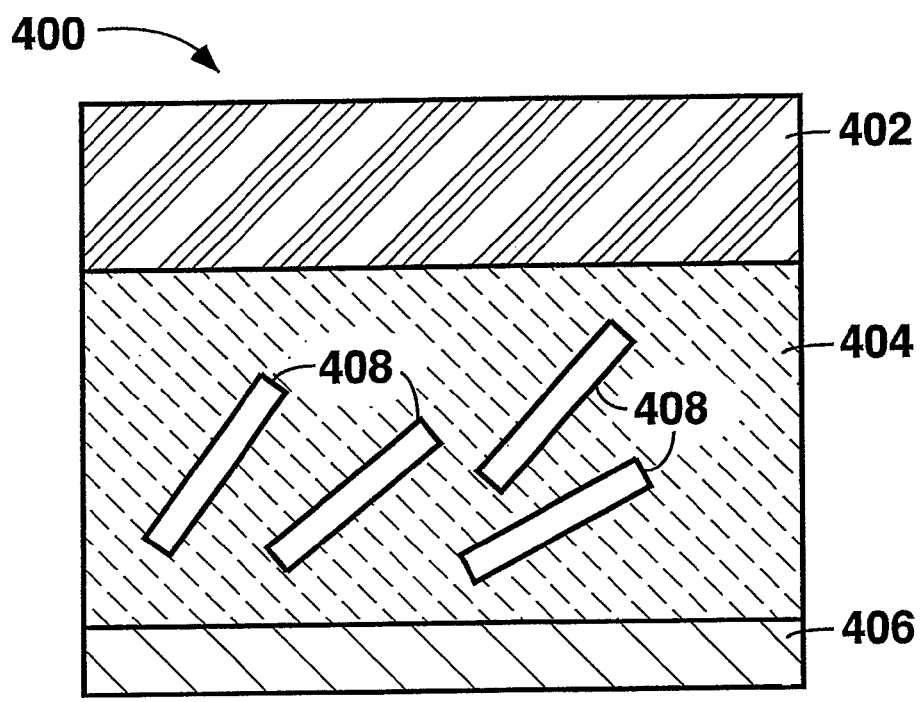
FIG. 4 shows a diagram of a surface coating according to various embodiments of the present invention.

In various embodiments, the number of observed reflectance directions may be chosen based on a desired resolution of results and/or the complexity of the surface to be measured. For example, each layer and/or materials contained in the layers of a surface may have a number of physical properties (e.g., roughness, local slope, curvature, real and imaginary portions of the index of refraction, etc.). In various embodiments, it may only be necessary to measure a minimum number of reflectance directions to obtain enough independent relationships to solve for all desired variables. For example, a minimum number of observed reflectance directions may be chosen according to the following:

$$\text{Minimum Number of Reflectance Directions} = 2L + M \quad (1)$$

where L is the number of physical layers of the surface through which light can potentially scatter, and M is the number of different materials contained in the layers (e.g., pigments, metallic flakes, etc.). For example, FIG. 4 shows an exemplary surface 400 that may be observed according to various embodiments. The surface 400 has a specialty coating, such as, for example, an interference or pearlescent coating, discussed above. The surface 400 includes three layers, clear coat 402, pigment layer 404 and substrate 406, as well as one material contained in the layers (e.g., metal flakes 408). Accordingly, a minimum number of observed reflectance directions for the surface 400 would be seven. It will be appreciated that useful readings may be obtained using less than the minimum number of reflectance directions according to Equation 1, however, in that case, the observed reflectance may not capture the contribution to BRDF from each of the surface features.

As the number of observed discrete reflectance directions is increased, the quality of the results obtained may also increase. For example, in various embodiments, additional physical properties may be measured. It will be appreciated however, that increasing the number of observed discrete reflectance directions will also increase the complexity, time necessary to observe at all reflectance directions, and noise. Accordingly, in various embodiments, it may not be necessary to observe more reflectance directions than the following:

$$\text{Maximum Number of Reflectance Directions} = 6L + 6M \quad (2)$$

where L and M are defined as above. Equation 2 may define the number of reflectance directions necessary to have an independent relationship for each physical property to be measured.

Figure 5:
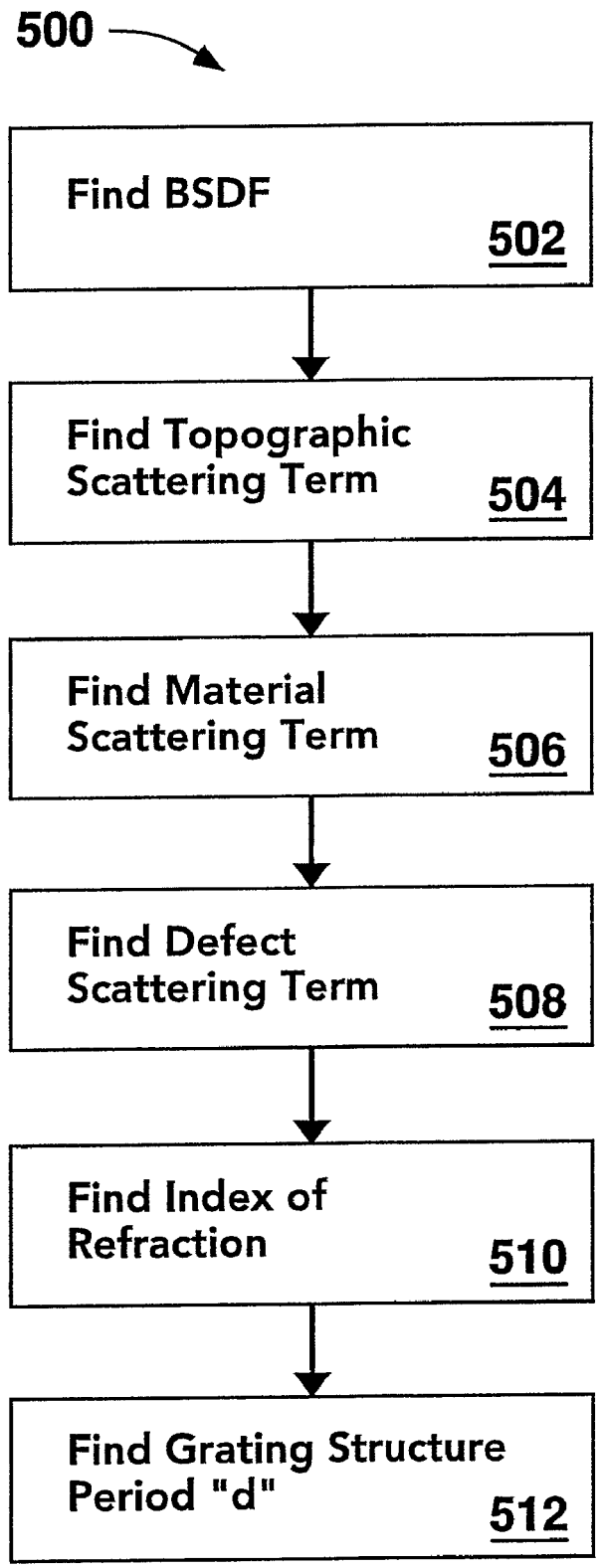
FIG. 5 shows a flow chart illustrating a process flow according to various embodiments of the present invention.

Referring back to FIG. 1, at step 106, the reflectance measured at step 104 may be processed to generate an appearance property or properties of the surface. The spatially undersampled BRDF itself may be considered an appearance property of the surface, though it will be appreciated that other appearance properties may be generated, for example, by manipulating the BRDF. At least one of the appearance properties may reflect directional differences in the appearance of the surface that are inherent in the measured reflectance intensities and directions. In various embodiments, additional appearance properties may be found by performing manipulations to the BRDF. For example, FIG. 5 shows a process flow 500, described below, for processing measured reflectance by plugging the measured reflectance into a mathematical model for the BRDF of the surface and performing certain mathematical manipulations. As another example, FIG. 8 shows a process flow 800 for analyzing various moments of the BRDF data.

The appearance properties generated at step 106 may yield information about the composition and features of the surface under measurement (e.g., physical properties). For example, in the coatings industry, properties of the formulation and application process of any coatings present on the surface may be found. For some physical properties, closed form solutions may exist that allow values for the properties to be derived directly from the measured reflectance or BRDF. For example, as discussed below, a grating structure period may be derived from the BRDF, and may relate directly to the distance between regularly spaced features of the surface. Also, some physical properties may be derived using experimental methods. For example, appearance properties of surfaces with known physical properties may be measured. A database may then be created showing correlations between appearance properties and physical properties. When a surface with unknown physical properties is measured, appearance properties (e.g., BRDF, and/or values derived therefrom) may be compared to the database to find the unknown physical properties.

FIG. 5 shows the process flow 500 for processing measured reflectance (e.g., BRDF) and deriving additional appearance properties of the surface using mathematical models based on the BRDF. Referring to FIG. 5, at step 502, the BRDF may be converted to a Bidirectional Scatter Distribution Function (BSDF). The BSDF represents the portion of the BRDF due to scattering of incident light. To calculate the BSDF, the specular component of BRDF is subtracted from the BRDF. The specular component is that portion of the BRDF that is due to Fresnel reflection of incident light. The specular component is concentrated in a reflectance direction that is related to the illumination direction such that the angle of incidence of the illumination direction is equal to the angle of reflectance of the specular reflectance direction. For example, referring to FIG. 3, the illumination direction 304 forty-five degrees from the surface and 45 degrees from the surface normal. Accordingly, the specular component is directed in reflectance direction 306, which is also 45 degrees from the surface and surface normal. It will be appreciated that if there is more than one illumination direction, then the specular component may be concentrated in more than one angle.

The specular component may be subtracted from the BRDF in a number of different ways. For example, one of the observed reflectance directions may be the specular direction. In this case, the BSDF may be found by subtracting the contribution of this reflectance direction from the overall BRDF. In embodiments where the specular direction is not one of the observed reflectance directions, then the specular component may be approximated based on the responses at observed reflectance directions near the specular direction. The approximation of the specular component may then be subtracted from the BRDF.

Referring again to FIG. 5, a topographic scattering term of the BSDF may be found at step 504. It will be appreciated that the BSDF may be expressed as:

$$BSDF = (16\pi^2/\lambda^4)\cos^2\theta_i \Phi_{ba}(\phi_s) R_a(\theta_i) S_z(f) \quad (3)$$

where $S_z(f)$ is the two dimensional Power Spectral Distribution (PSD) of any height fluctuations (Z) of the surface. Accordingly, dividing the BSDF by $(16\pi^2/\lambda^4)\cos^2\theta_i$ yields a topographic scattering term that is proportional to height fluctuations on the surface.

At step 506, a material scattering term may be found. The material scattering term may be indicative of fluctuations in the composition or density of the surface material (e.g., homogeneity, bubbles, inclusions, randomly dispersed or distributed pigments smaller than approximately 30 microns, etc.). It will be appreciated that the BSDF may be expressed as:

$$BSDF = (1/\lambda^2)\Phi_{ba}(\phi_s) R_a(\theta_i) S_m(f) \quad (4)$$

where $S_m(f)$ is the PSD of the perturbation of the material response for scattering. This PSD may be related to specific models of the material inhomogeneities, such as the magnitudes and spatial distribution of variations in composition. A material scattering term may then be found by dividing the BSDF by $(1/\lambda^2)$. Experimental methods may be used to tie values of the material scattering term (e.g., an appearance property) to particular types, sizes, etc. of fluctuations in composition and/or density of the surface (e.g., physical properties).

At step 508, a defect scattering term of the BSDF may be found. Defect scattering occurs when a surface feature or bulk property perturbation is localized and/or isolated spatially (e.g., pits or bumps in the surface, individual inclusions in an otherwise homogeneous bulk material). It will be appreciated that, if the defects are randomly distributed, then the BSDF may be expressed as:

$$BSDF = (1/\lambda^2)\Phi_{ba}(\phi_s) R_a(\theta_i) S_d(f) \quad (5)$$

where $S_d(f)$ is the PSD of the collection of defects in the surface. Accordingly, a defect scattering term may be calculated by dividing the BSDF by $(1/\lambda^2)$. Experimental methods may be used to tie particular values of the defect scattering term to particular defect types and locations. It will be appreciated from comparing Equations 4 and 5, that $S_d(f)$ and $S_m(f)$ may have the same value. Accordingly, Equation 4 may be applied to a surface that is measured or assumed to be relatively free of blemishes. On the other hand, Equation 5 may be applied to surfaces with known defects.

Figure 6:
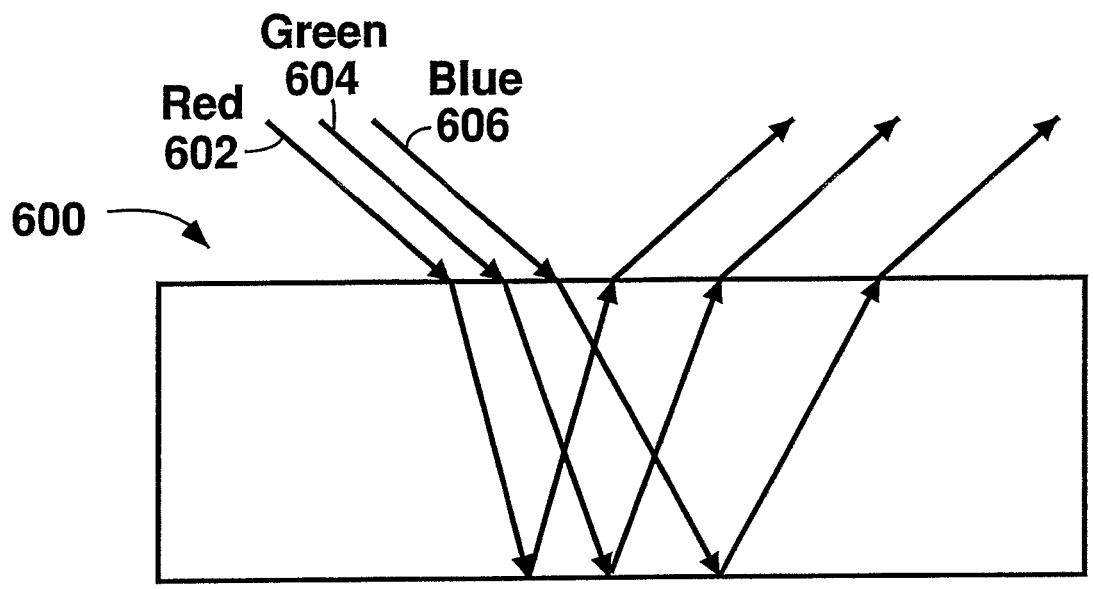
FIG. 6 shows a diagram of refraction by a surface according to various embodiments of the present invention.

At step 510, an index of refraction of the surface may be found. FIG. 6 shows a surface 600 having red 602, green 604, and blue 606 beams incident thereon. FIG. 6 illustrates how refraction may cause the different beams 602, 604, 606 to behave differently. Snell's law may be used to find the index of refraction of the surface as follows:

$$n_1 \sin\theta_1 = n_2 \sin\theta_2 \quad (6)$$

where $n_1$, is the index of refraction of the surface, $n_2$ is the index of refraction of the medium between the surface and the observation points, $\theta_1$, is the angle of the illumination direction and $\theta_2$ is the refraction angle at a given wavelength. The index of refraction may be considered a physical property of the surface, however, it will be appreciated that additional physical properties (e.g., the grating structure period below) may be derived based on the index of refraction.

Figure 7:
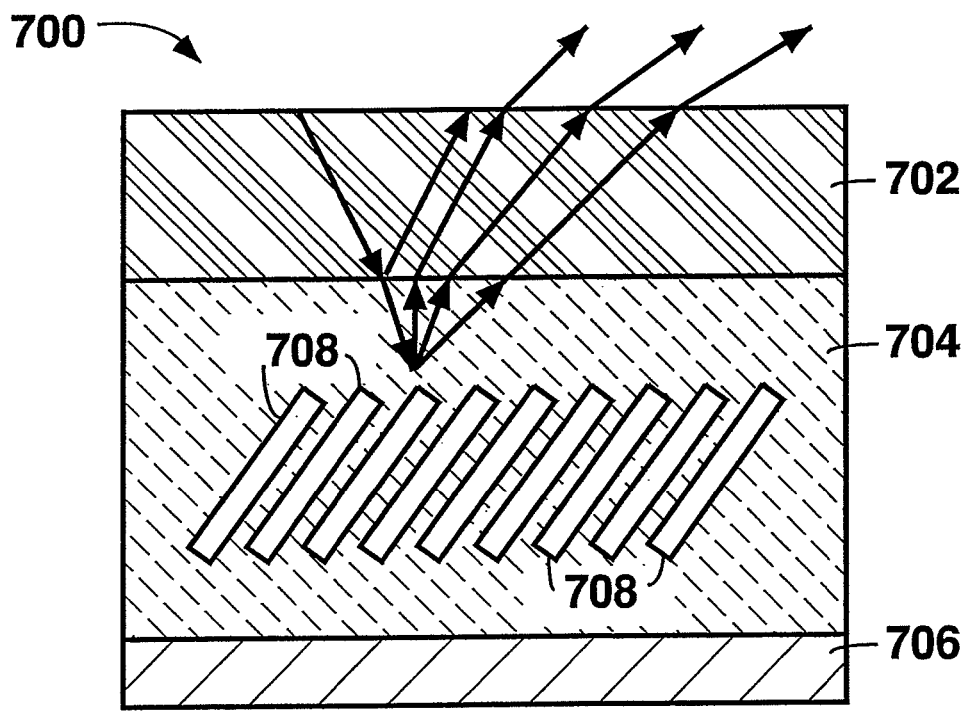
FIG. 7 shows a diagram of diffraction and/or interference by a surface according to various embodiments of the present invention.

At step 512, a grating structure period of the surface may be found. The grating structure period may provide information about surface features, interface features, bulk material structure, pigments, particles, flakes, etc., present in the surface that have an ordered structure. Such ordered features may cause diffraction and/or interference in reflected light based on the grating structure period of the features. For example, FIG. 7 shows an exemplary surface 700 having a series of flakes 708 embedded therein at a regular or semi-regular interval and orientation. Note that the surface 700 may include a plurality of layers 702, 704 and 706. The grating structure period of the surface 700 may reflect the distance between and/or orientation of the flakes 708. The grating structure period may be found as follows:

$$A = 2nd\sin(\theta) \quad (7)$$

where n refractive index of the surface, d is the period of the grating line structure and θ is the angle at which the wavelength of light is diffracted normal to the grating line structure.

FIG. 8 shows a process flow 800 for deriving values indicative of surface properties using a moment or moments of the BRDF. At step 802 a first moment, or weighted directional response may be found. The weighted direction response may be the vector summation of all of each of the vectors representing the observed intensities and reflectance directions over a given wavelength or wavelength range. It will be appreciated that where multiple wavelengths or wavelength ranges are considered, a weighted directional response may be calculated for each of the considered wavelengths or wavelength responses.

In various embodiments, weighting factors may be applied to one or more of the observe reflectance directions. For example, the weighting factors may be chosen so that the resulting weighted BRDF more closely approximates a geometrically uniform distribution of reflectance directions. In various embodiments, weighting factors may be chosen to accentuate reflectance directions that have increased significance for certain surface types. For example, when the surface includes an interference pigment, the reflectance direction having an aspecular angle of −15° may be disproportionately weighed, when the surface includes a retroreflective material, reflectance directions having aspecular angles of 75° and 110° may be disproportionately weighted.

Also, in various embodiments, weighting factors may be chosen to be compatible with various standards. For example, the DIN 6175-2 standard defines color difference formulas with weighting functions that depend on the standard measurement angles, (e.g., the 15/25/45/75/110 angles described above). In various embodiments, the weighting factors may be chosen based on human perceptual studies (e.g., the reflectance directions that humans most strongly perceive may be given higher weighting factors).

It will be appreciated that the weighting factors may also be chosen to more accurately represent the distribution of energy reflected off the surface. For example, if the total energy reflected off the surface is 20 mW, and it is expected that a disproportionately high portion of the 20 mW is expected to be reflected in a certain range of reflectance directions, then intensity measurements taken in that range of reflectance directions may be given a relatively higher weighting compared to other directions. In this way, the spatially under-sampled BRDF may more closely match the actual energy distribution modeled by the full BRDF.

The weighted directional response may be tied to various properties of the surface. For example, in the case of a surface having a coating, the weighted directional response may be used to identify application process variations between two surfaces. For example, when two surfaces differ only in the application process of a coating on the surfaces, the weighted directional response of the first surface can typically be transformed into the weighted directional response of the second surface. The necessary translations, rotations and scaling can be experimentally tied to particular application process variations.

At step 804, a mean spectral first moment of the surface may be found. The mean spectral first moment may be a vector whose direction represents the average spectral first moment. A weighted spectral spatial distribution function may be found at step 806. The weighted spectral spatial distribution may be a function that describes the general line shape defined by the directional endpoints of the weighted directional response. Both of these appearance properties (e.g., the mean spectral first moment and weighted spectral spatial distribution) may be experimentally tied to various physical properties of the surface.

Figure 9:
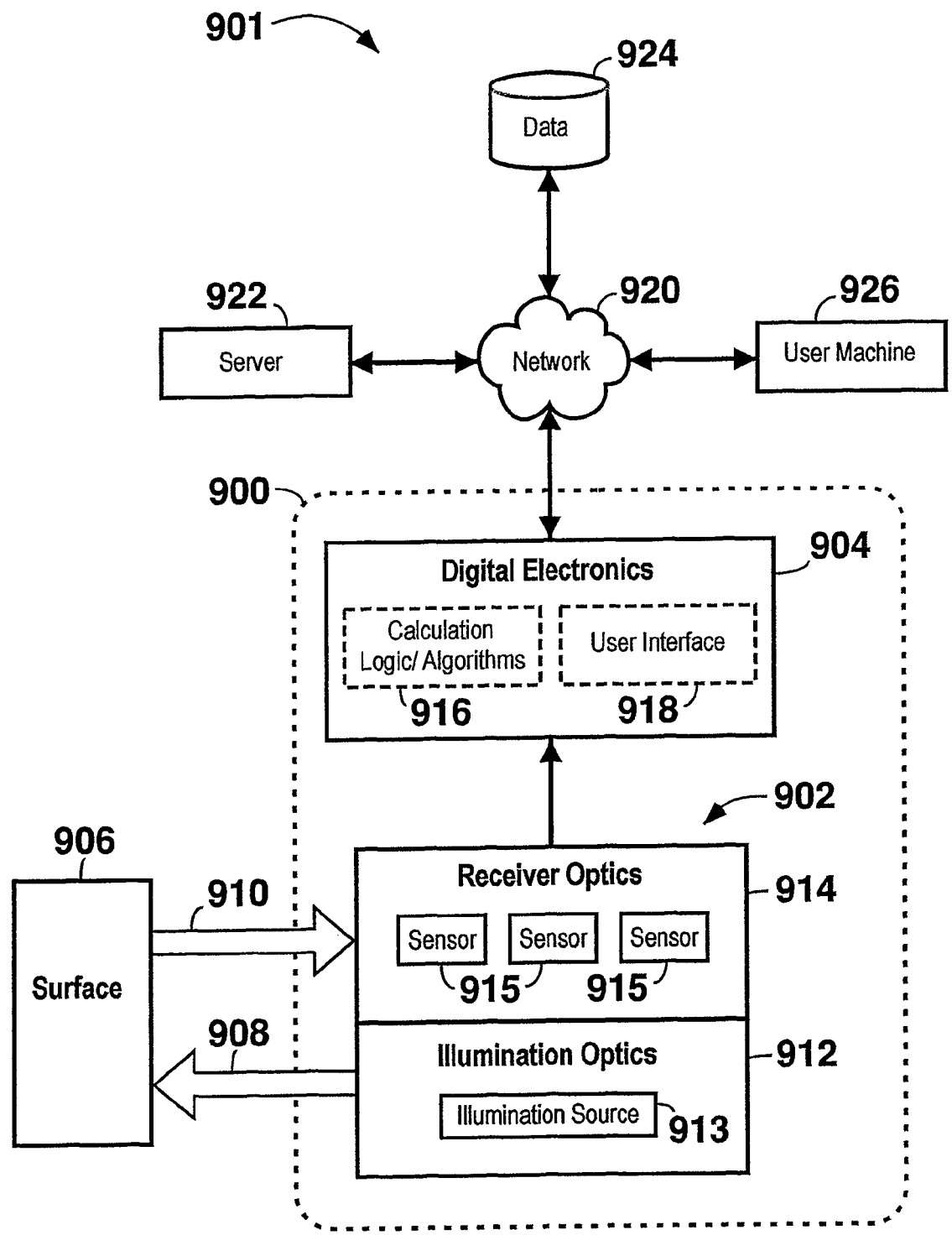
FIG. 9 shows a diagram of a system according to various embodiments of the present invention.

FIG. 9 shows a diagram of a system 901 that may be used to implement methods of measuring and/or analyzing a spatially under-sampled BRDF of a surface, for example, as described above, according to various embodiments. The system 901 includes a measuring device 900, and may also include various other information storage, processing and/or interface devices such as, for example, a server 922, a user machine 926 and/or a database 924. The various devices 900, 922, 924, 926 of the system 901 may be in contact with one another via a network 920, which may be any suitable type of wired or wireless network.

In various embodiments, the measuring device 900 may include an optics unit 902 and an electronics unit 904. The optics unit 902 may include illumination optics 912 configured to direct light 908 towards a surface 906 under inspection, and receiver optics 914 for receiving and sensing the reflectance 910 of the light 908 off of the surface 906. For example, the illumination optics 912 and receiver optics 914 may sense a spatially under-sampled BRDF of the surface 906 as described above. The electronics unit 904 may process the reflectance results generated by the optics unit 902. In various embodiments, the electronics unit 904 may include calculation logic 916 for deriving appearance properties of the surface and/or relating appearance properties to physical properties. A user interface module 918 may present results (e.g., raw reflectance data, appearance properties, physical properties, etc.) to a user of the device 900. In various embodiments, some or all of the processing and presenting of results may be performed by other components of the system for processing (e.g., server 922, database 924, user machine 926). For example, the server 922 and/or user machine 926 may perform processing to derive appearance and/or physical properties; results of the processing may be presented to a user through the user machine 926; and the database 924 may store experimental correlations between measured reflectance and surface properties.

Referring back to the optics unit 902, the illumination optics 912 may include one or more illumination sources 913 configured for directing light 908 toward the surface 906 from one or more illumination directions. The illumination sources 913 may include any kind of suitable illumination source including, for example, an incandescent source, a white LED, etc. In various embodiments, each illumination source 913 may include a plurality (e.g., nine) LED's of various spectral outputs. The LED's may be positioned on a leadless chip carrier or any other kind of installation technology. It will be appreciated that the illumination source or sources 913 may generate light across the wavelengths that are to be measured by the receiver optics 914 as described herein below. In various embodiments, the illumination sources 913 may be configured to generate collimated or non-collimated beams, for example, as described above.

Figure 16:
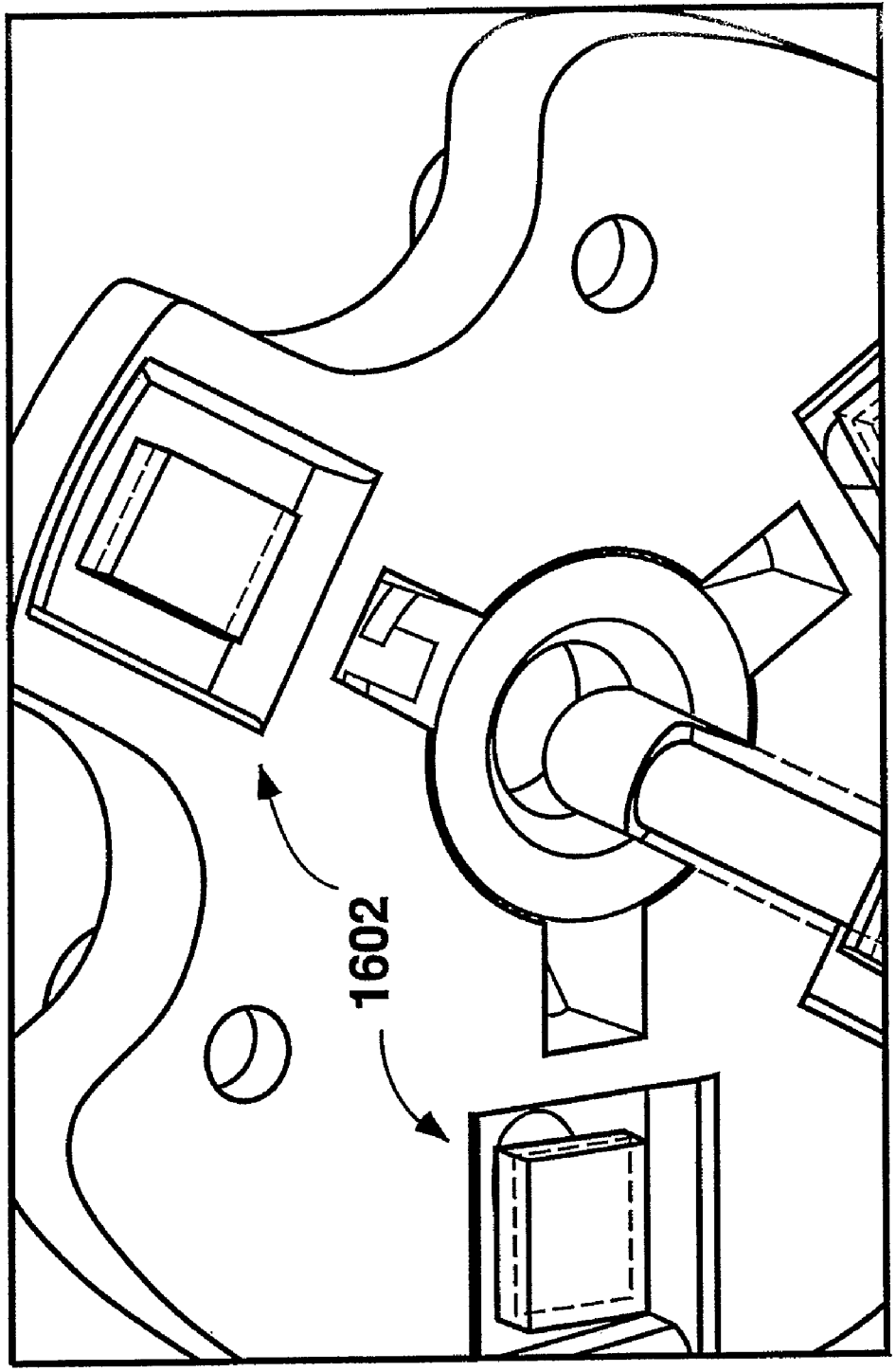
FIG. 16 shows various sensors according to various embodiments of the present invention.

The receiver optics 914 may include one or more sensors 915 positioned along discrete reflectance directions. In various embodiments, the sensors 915 may be positioned to sense non-coplanar reflectance directions such as, for example, reflectance directions 206, 208 and 210 shown in FIG. 2. The sensors 915 may be any kind of imaging or non-imaging sensor or sensor assembly suitable for measuring reflectance (e.g., across multiple discrete wavelength ranges). For example, the sensors 915 may include one or more photodiodes. Any suitable kind of wavelength discriminating equipment (e.g., any kind of band-pass spectral filter, diffraction grating spectrograph, etc.) may be placed in front of the photodiode to sense discrete wavelength ranges. For example, the MAZet Jencolour product line may be used, as shown by sensors 1602 in FIG. 16. In various embodiments, a wheel or other movable device including multiple bandpass filters may be selectively placed in front of the photodiode, allowing one photodiode to measure several discrete wavelength ranges. In other various embodiments, multiple photodiodes may be provided along each reflectance direction, which each of the multiple photodiodes having a separate band-pass filter. It will be appreciated that the sensors 915 may include a wide-band detector capable of discretely measuring multiple wavelength ranges simultaneously such as, for example, a RGB sensor, such as a camera with a logarithmic response or a small array of pixels (e.g., the TCS230 line available from Taos, Inc.).

Figure 10:
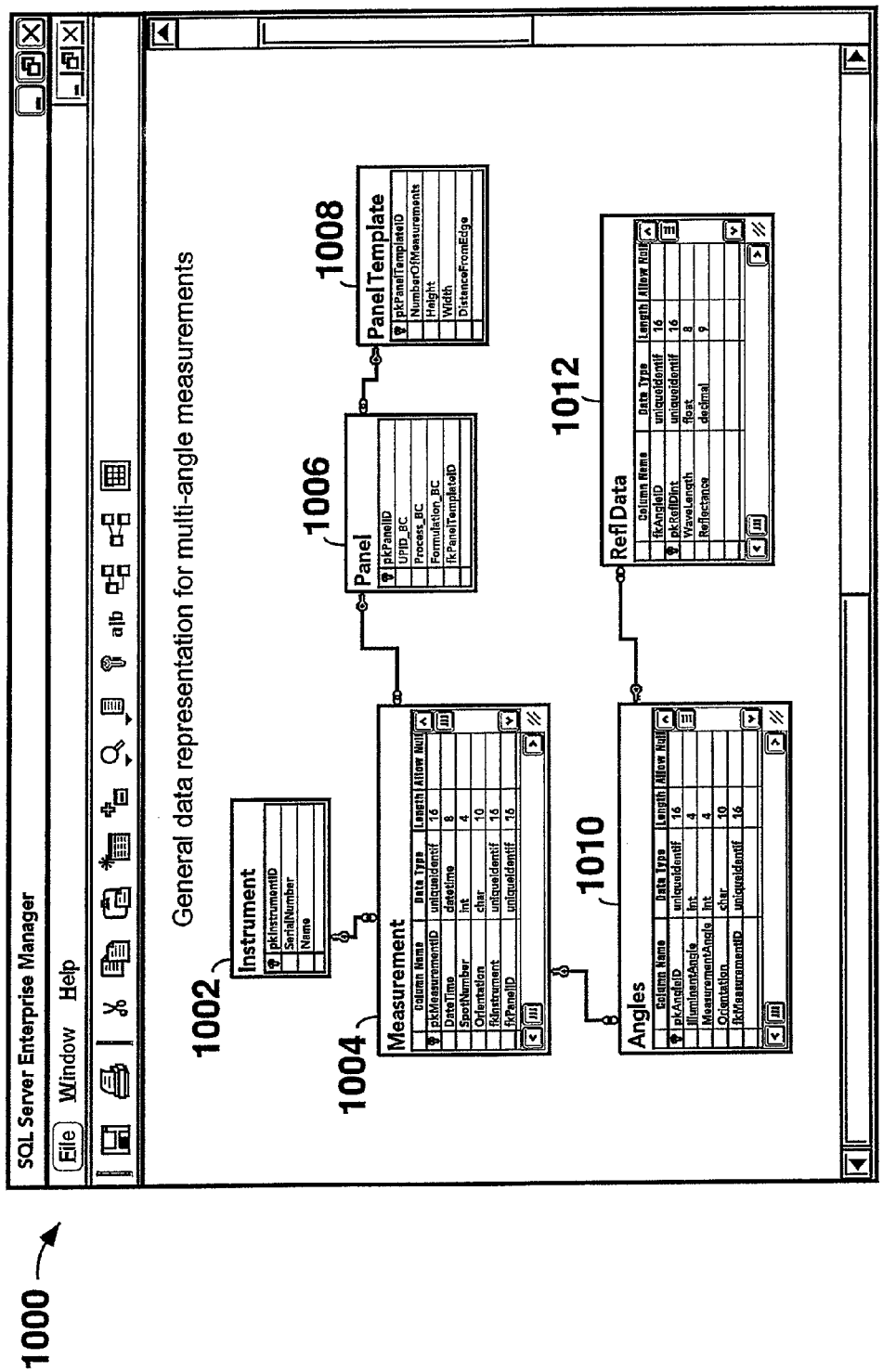
FIG. 10 shows a user interface that may be presented to a user according to various embodiments of the present invention.
Figure 11:
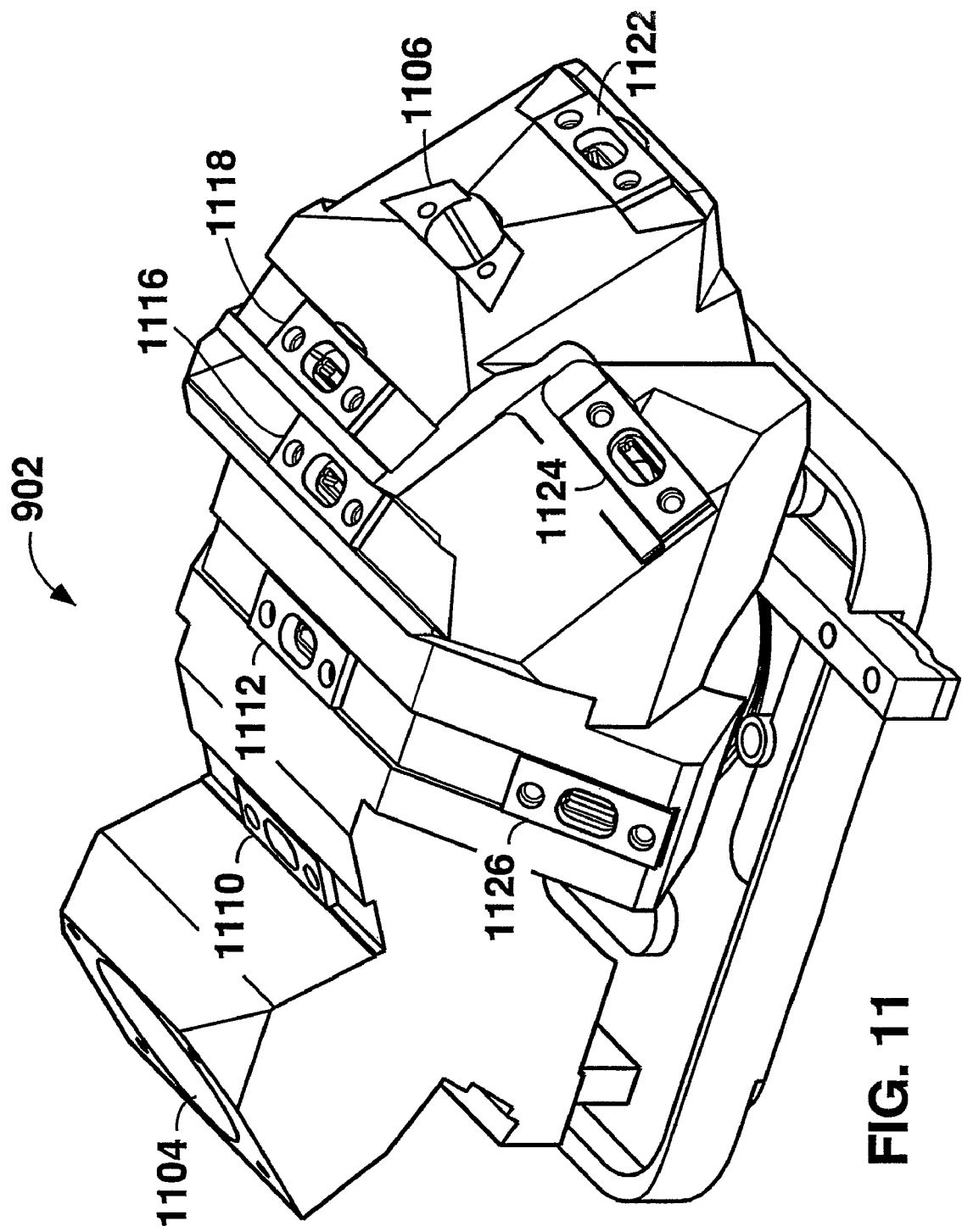
FIGS. 11-14 shows three-dimensional views of an apparatus according to various embodiments of the present invention.
Figure 12:
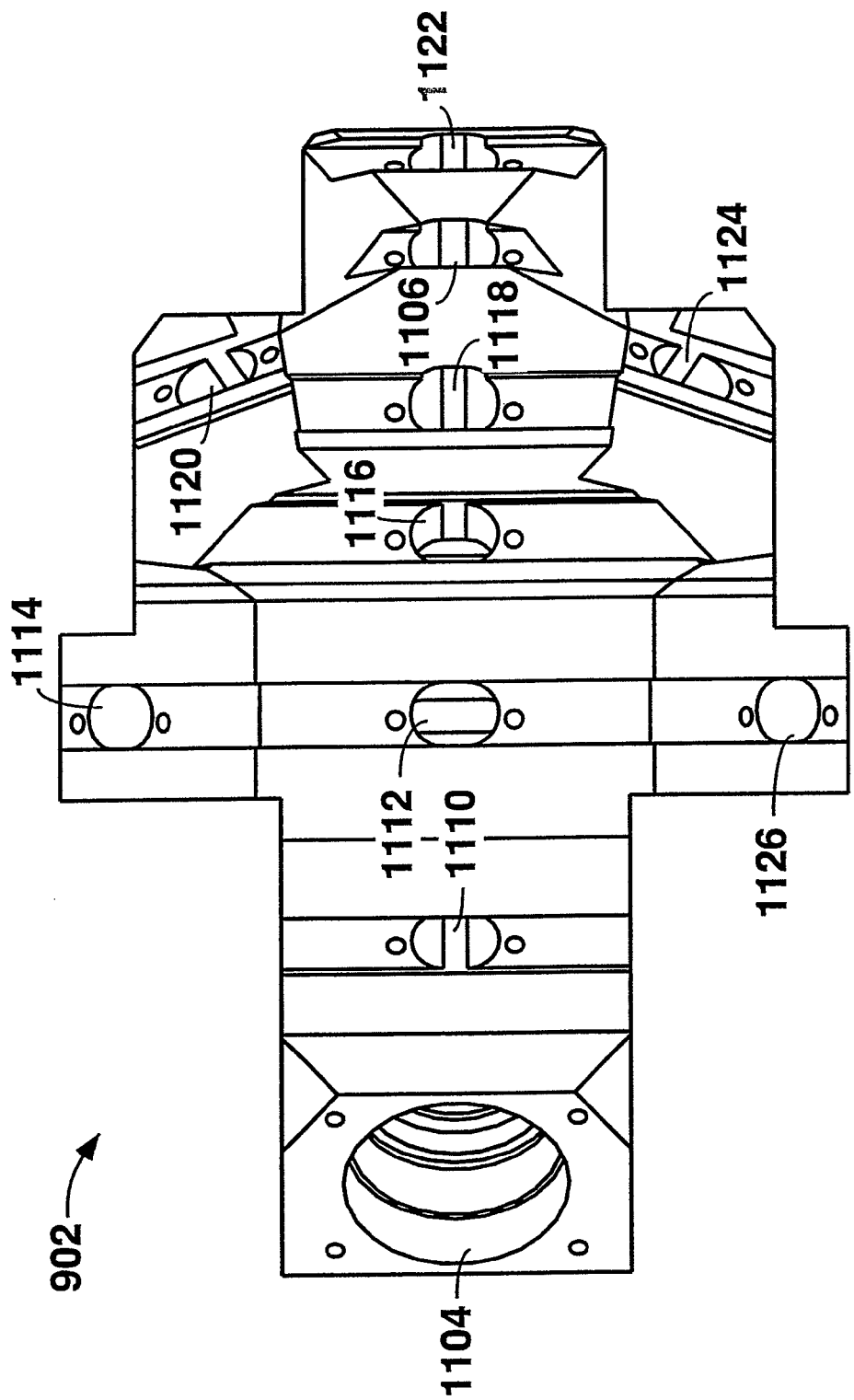
Figure 13:
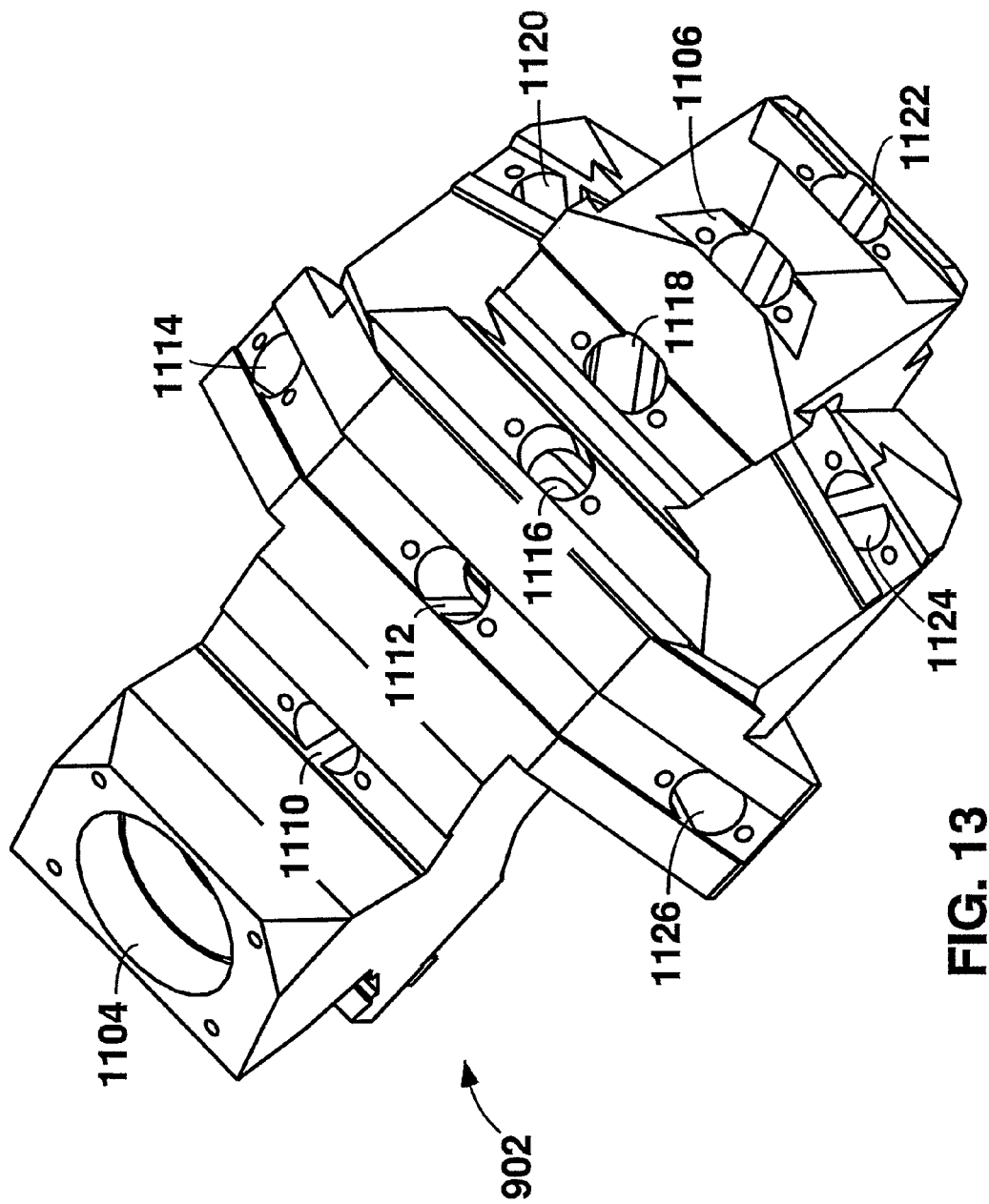
Figure 14:
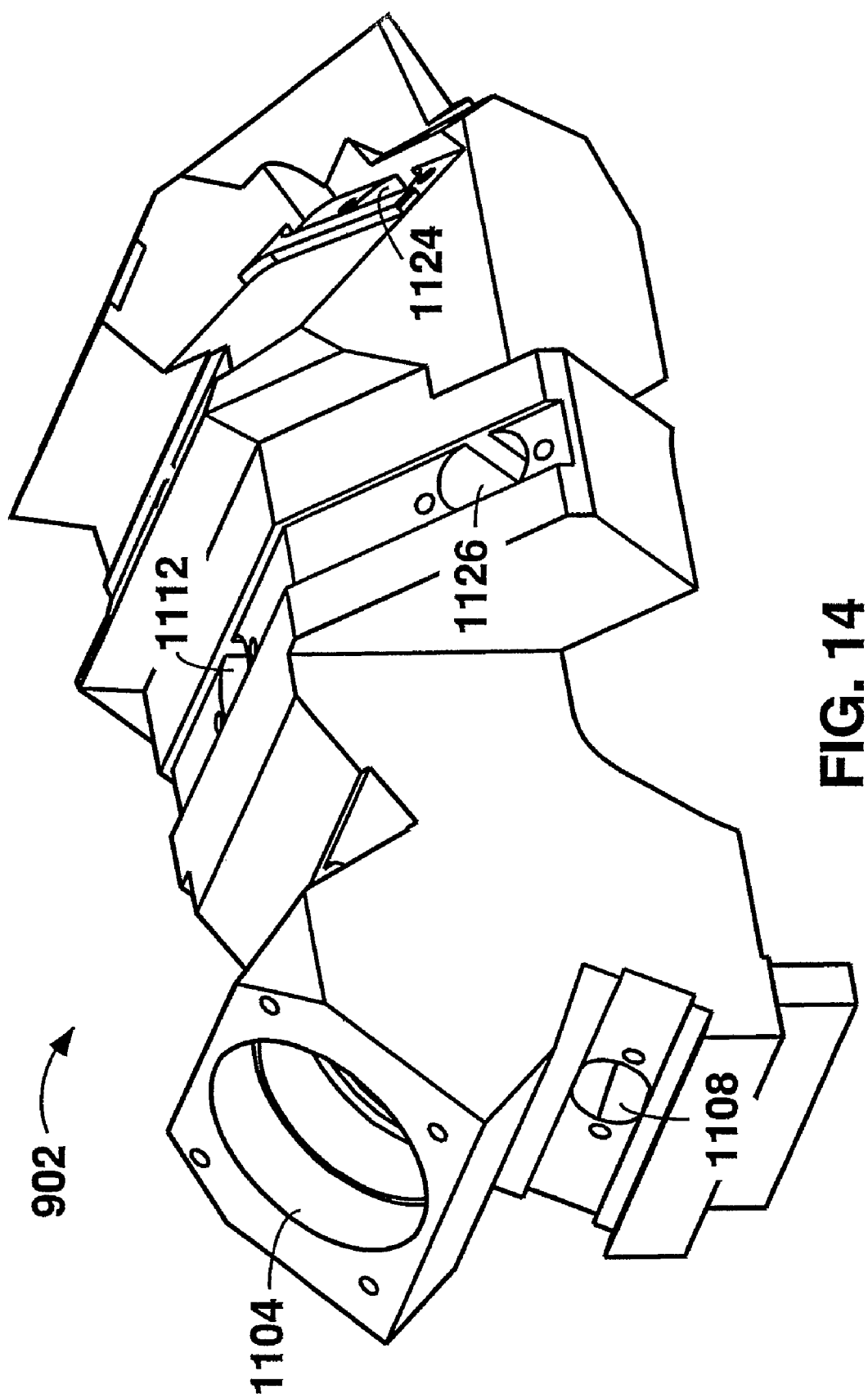

FIG. 10 shows an exemplary database schema 1000 that may be used to store measurement data, for example, at database 924 and/or electronics unit 904. Box 1002 may include information about the instrument (e.g., instrument 900) that is taking the measurement. Such information can include a name, serial number, etc. Box 1004 may include information about a particular measurement including, for example, date, time, location number, instrument orientation, etc. Boxes 1006 and 1008 may include information about the panel or surface under measurement. For example, box 1006 may include information about the panel or surface itself while box 1008 may include a template of preferred measurements to be taken on the surface (e.g., the number, height, width, distance from the edge, etc.). Box 1010 may include information about each of the angles or reflectance directions that are to be observed, and box 1012 may include actual measured data. For example, if eleven reflectance directions are measured over thirty-one wavelength ranges, then the total number of data points for each measurement may be 341.

FIGS. 11-14 show views of an exemplary optics unit 902 according to various embodiments. The exemplary optics unit 902 includes one illumination source 1104 and eleven apertures or pupils for receiving sensors 1106, 1108, 1110, 1112, 1114, 1116, 1118, 1120, 1122, 1124, 1126. It will be appreciated that sensor may comprise an aperture for receiving light and a receiving element for sensing the intensity of the light. In the exemplary unit 902, the illumination source 1104 is directed toward a surface positioned below the unit (not shown) at a forty-five degree angle relative to the surface normal. Accordingly, the specular reflectance direction is also at a forty-five degree angle relative to the surface normal. Pupil 1106 may be positioned to sense reflectance at the specular reflectance direction.

In various embodiments, the positions of the other pupils may be expressed relative to the specular reflectance direction, although, it will be appreciated that the positions of the pupils may be expressed in any suitable coordinate system. For example, pupil 1122 may be positioned at $-15°$ relative to the specular. Pupil 1118 may be at $15°$ relative to the specular, with pupil 1116 at $25°$, pupil 1112 at $45°$, pupil 1110 at $75°$, and pupil 1108 at $110°$. The location of pupils off the plane of pupils 1106, 1108, 1110, 1112, 1116, and 1118 may also be expressed relative to the specular reflectance direction. For example, pupil 1124 is positioned $25°$ from the specular reflectance direction and rotated $90°$ counterclockwise out of plane. Similarly, pupil 1120 is positioned $25°$ from the specular reflectance direction and rotated $90°$ clockwise out of plane. Pupils 1114 and 1126 are both positioned $60°$ from the specular reflectance direction and rotated $54.7°$ clockwise and counterclockwise out of plane, respectively.

Figure 15:
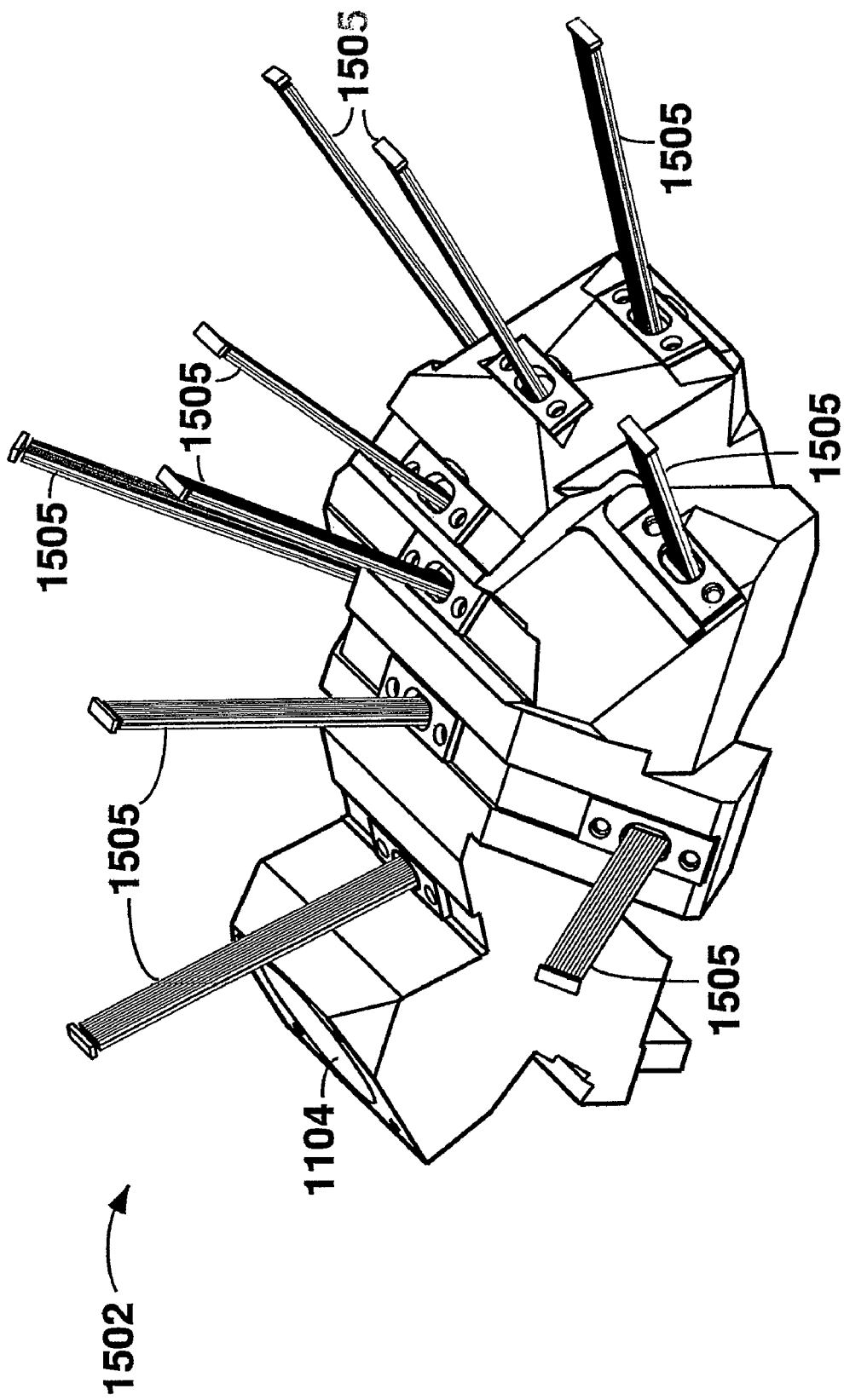
FIG. 15 shows a three-dimensional view of an apparatus according to various embodiments of the present invention.

It will be appreciated that although eleven pupils for sensors are shown, any suitable number of sensors may be used. Also the sensors may be placed to receive any suitable reflectance directions, for example, reflectance directions that are non-coplanar. Also, in various embodiments, the sensors may be positioned at in the various pupils of the optics unit 902. In other various embodiments, some or all of the sensors may be positioned remote from the pupils. For example, FIG. 15 shows another exemplary optics unit 1502 having optical fibers 1505 originating at various pupils. The fibers 1505 may transport light incident at the pupils to a remote location (not shown) that may house one or more receiving elements.

Figures 17, 18:
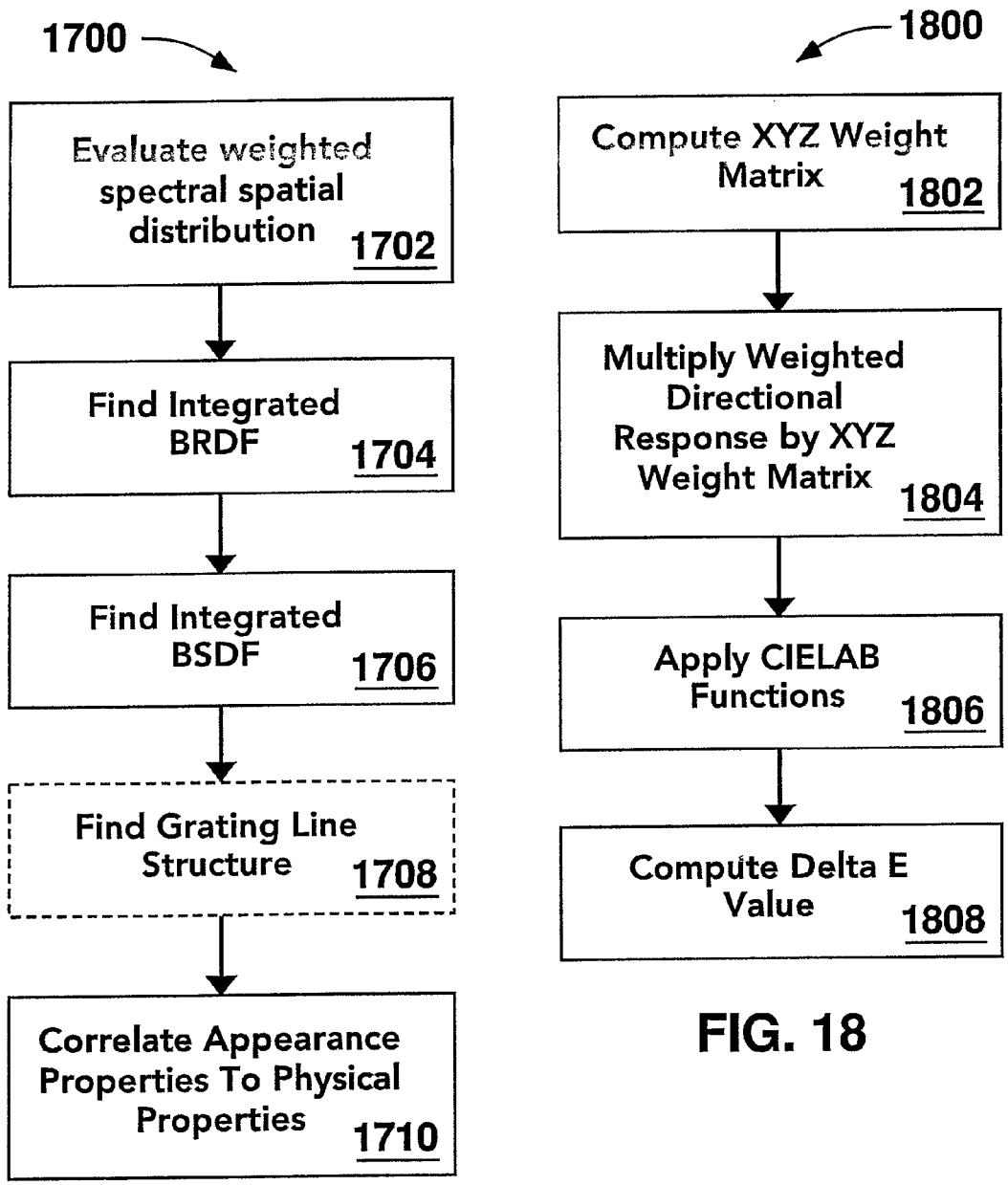

FIG. 17 shows an exemplary process flow 1700 for identifying properties of an unknown surface using the methods and/or apparatuses described above. At steps 1702, 1704, 1706, and 1708, various appearance properties may be derived from the observed reflectance or BRDF of the surface. For example, at step 1704, a magnitude of the weighted spectral spatial distribution may be found. At step 1704, an integrated BRDF of the surface may be found. An integrated BSDF of the surface may be found at step 1706. In various embodiments, a grating line structure of the surface may be found at step 1708. At step 1710, the appearance properties are compared to a look-up table, such as look-up Table 1, below to identify the unknown surface and/or physical properties thereof. It will be appreciated that the look-up table may be stored, for example, by the database 924 and/or the electronics unit 904 of the device 900.

TABLE 1

| Surface Type & Properties | Weighted Spectral Spatial Distribution Magnitude | Integrated BRDF | Integrated BSDF | Grating Structure Line | Moment Size | Diffuse/ Specular |
| --- | --- | --- | --- | --- | --- | --- |
| Specular Absorber | Small | Small | Small | N/A | N/A | Specular |
| Pigmented Surface | Small | Small | Large | N/A | Medium | N/A |
| Surface Texture Absorber | Small | Small | Large | N/A | Small | N/A |

TABLE 1-continued

| Surface Type & Properties | Weighted Spectral Spatial Distribution Magnitude | Integrated BRDF | Integrated BSDF | Grating Structure Line | Moment Size | Diffuse/ Specular |
|---|---|---|---|---|---|---|
| Specular Pure Absorber | Small | Large | Small | N/A | N/A | N/A |
| Heavy Surface Structure | Large | Small | Small | Yes | N/A | N/A |
| Metal Flake | Large | Small | Large | No | N/A | N/A |
| Special Effect - Chroma Flair | Large | Small | Large | Yes | N/A | N/A |
| Special Effect - Mica | Large | Large | Small | No | N/A | N/A |
| Surface Scratches | Large | Large | Small | Yes | N/A | N/A |
| Special Effect - Chroma Flair | Large | Large | Large | Yes | N/A | N/A |
| Potential Calibration Error | Large | Large | Large | No | N/A | N/A |
| Potential Calibration Error | Small | Small | Small | N/A | N/A | Diffuse |
| Potential Calibration Error | Small | Large | Large | N/A | N/A | N/A |
| Undetermined | Large | Small | Small | No | N/A | N/A |

FIG. 18 shows a process flow 1800 for using the processes and/or apparatuses described above to find a directional color difference between two surfaces according to various embodiments. In the process flow 1800, the directional color difference is a Delta E value computed according to the CIELAB equations, though it will be appreciated that any suitable color measurement methodology may be used. At step 1802, an XYZ weight matrix may be computed based on a specified illuminant and observer. The XYZ weight matrix may be of size 3 by X, where X is the number of discrete wavelengths or wavelength range that are measured. Recall that the weighted directional response can be represented by a set of vectors, with one vector for each wavelength range. Accordingly, the weighted directional response may be represented as a vector of size X by d, where d is the number of terms necessary to represent the spatial coordinate axis (e.g., in three dimensions, d is equal to 3). The two matrices may be multiplied at step 1804 resulting in a 3 by d matrix. The CIELAB functions may be applied at step 1806. In various embodiments, the CIELAB functions may be applied to each column of the 3 by d matrix individually. Alternatively, the CIELAB functions may be applied to the magnitude of each column of the 3 by d matrix. At step 1808, the Delta E value may be calculated.

Figures 19, 20:
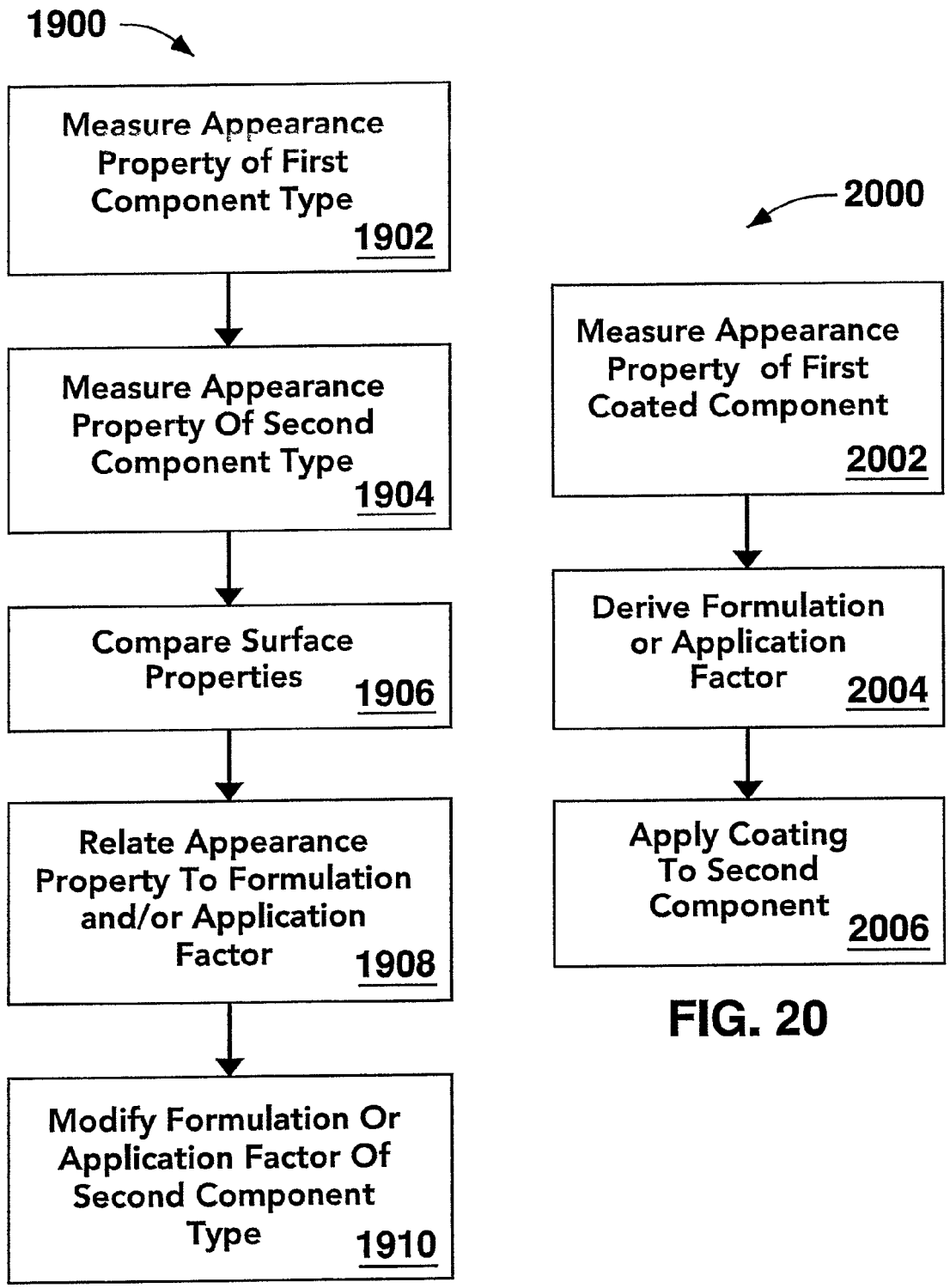

FIG. 19 shows a process flow 1900 that may be utilized in the coatings industry, for example, by a finisher of automotive parts, to match the appearance of coatings applied to two components, which may be manufactured and coated at different times and different facilities (e.g., a door handle may be made at Factory A, while a bumper may be made at Factory B). The process flow 1900 may be used to determine coating formulation and/or process factors for the second component based on observations of the first component. At step 1902, an appearance property of a first coated component may be measured and/or calculated. The appearance property may be, for example, a weighted directional response, BRDF, etc. At step 1904, an appearance property of a second coated component may be measured, for example in the same way as the first. At step 1906, the appearance properties of the two coated components may be compared. If differences are found, (e.g., because the second coated component does not match the first) then the appearance property exhibiting the differences may be tied to a particular formulation or application factor at step 1908, for example, as described above. The formulation or application factor of the second coated component may then be modified, at step 1910, to coat additional components to match the first, allowing a higher quality appearance match between components.

FIG. 20 shows a process flow 2000 for determining process and/or formulation factors to be used when coating a replacement part. At step 2002, an appearance property of a first coated component may be found (e.g., a weighted directional response, BRDF, etc.). The first coated component may be, for example, a component of an automobile. At step 2004, a formulation or application factor for reproducing the appearance of the coating on the first component may be found (e.g., by tying the appearance property to the formulation or application factor). At step 2006, a coating may be applied to a second component, considering the formulation or application factor found at step 2004. The process flow 2000 may be useful, for example, to autobody shops. In this way the coating of the second component may match that of the first. Using the process flow 2000, an autobody shop may match the paint formulation and process used to repaint a component or paint a replacement component to match the appearance of components already on the car. This may provide a better appearance match then reproducing the original formulation and process factors, as the appearance of the components changes with weathering and wear.

FIG. 21 shows a process flow 2100, according to various embodiments, for verifying the identity of a security component. The security component may be, for example, a security ink (e.g., a security ink having an appearance that depends on viewing angle). The ink may be present on a label or other indicator on a product. In various embodiments, the security component may be the product itself, for example, in the instance of a cosmetic or similar product having a distinct appearance. Referring to the process flow 2100, at step 2102, an appearance property of the first unknown component may be measured. The appearance property may be a weighted directional response, BDRF, etc. At step 2104, the measured appearance property may be compared to a known appearance property of an authentic security component. The authenticity of the product under test may be found at step 2106. For example, if the appearance property of the unknown security component matches the appearance property of the known product, then the unknown product is likely authentic. If the property of the tested security component does not match the known property, then the product may be counterfeit. It will be appreciated that the reliability of the match may be increased by considering multiple independent appearance properties.

FIG. 22 shows a process flow 2200 according to various embodiments, for identifying the source of a component. The process flow 2200 may be useful, for example, to forensic investigations. At step 2212, an appearance property of a component may be analyzed. The component may be, for example, an automobile body piece at the scene of a hit and run accident, a scrap of clothing left at the scene of a crime, or other component that is the subject of a forensic investigations. At step 2214, the appearance property of the component may be compared to similar properties of components of known origins. At step 2216, the component may be identified based on a match between the measured appearance property and the known appearance properties. For example, an automobile body piece may be tied to a particular make, model, production run, etc.

According to exemplary embodiments of the present disclosure, digital numerical analysis (DNA) may be employed to summarize and/or transform multiangle spectral data into a two or three dimensional spectral representation. DNA processing may be advantageously used to generate a weighted vector sum based on values for the various measurement directions, with the weights being determined and implemented based on reflectance factors for each direction. The result of this sum is a spectrum of points in 2D or 3D space, one point for each measured wavelength, which represent "fingerprint" values for the surface-of-interest. The weighted vector sum is also generally scaled by the length of the vector sum of an ideal white Lambertian reflector for enhance comparability of the fingerprint values for the surface-of-interest relative to typical reflectance values. In an exemplary implementation, the coordinate system for DNA consists of the specular direction (z axis), the projection of the illumination direction orthogonal to the specular direction (y axis), and the cross product of these two directions (x axis).

For purposes of the present disclosure, a measurement direction is described with reference to the angle it makes with the specular direction and by its angle of rotation about the specular axis from the positive y axis. A measurement with an illumination direction that makes an angle of $\Lambda°$ with surface normal, and a measurement direction that makes an angle of $\Phi°$ with specular, and has angle of rotation $\Theta°$ about specular, is described as $\Lambda as\Phi az\Theta$. The (x,y,z) coordinates of the measurement direction $\Lambda as\Phi az\Theta$ are then $(\sin(\Phi)*\sin(\Theta), \sin(\Phi)*\cos(\Theta), \cos(\Phi))$.

To further illustrate DNA processing and the applicability thereof for purposes of the present disclosure, an exemplary implementation thereof is described. Thus, for a measurement consisting of 10 directions, and 31 wavelengths with 1 0nm spacing from 400 nm to 700 nm, exemplary measurement directions are 45 as-15az0, 45as15az0, 45as25az-90, 45as25az0, 45as25az90, 45as45az0, 45as60az-54.7, 45as60az54.7, 45as75az0, and, 45as1 az0. The (x,y,z) coordinates and reflectance factors for these directions are (0, −0.26, 0.97), (0, 0.26, 0.97), (−0.42, 0.00, 0.91), (0, 0.42, 0.91), (0.42, 0.00, 0.91), (0, 0.71, 0.71), (−0.71, 0.50, 0.50), (0.71, 0.50, 0.50), (0, 0.97, 0.26), and (0, 0.94, −0.34), respectively.

The following Table 2 shows spectra and corresponding DNA coordinates for a hypothetical measured sample. Using the coordinates of the direction vectors set forth in the previous paragraph, the z coordinate is computed at 700 nm as 213*0.97+47.5*0.97+17*0.91+13.7*0.91+14.6*0.91+ 2.1*0.71+0.9*0.50+0.9*0.50+0.9*0.26+0.9*−0.34=39.5.

The exemplary embodiment of Table 1 includes measurements at sixteen (16) wavelengths. Greater (e.g., 31) or lesser measurement wavelengths may be employed according to the present disclosure to generate an appropriate fingerprint.

TABLE 2

| WL | 45as-15az0 | 45as15az0 | 45as25az-90 | 45as25az0 | 45as25az90 | 45as45az0 |
|---|---|---|---|---|---|---|
| 400 | 34.1 | 98.5 | 8.1 | 43.2 | 6.9 | 4.8 |
| 410 | 28.6 | 75.9 | 5.4 | 40.9 | 4.8 | 6.5 |
| 420 | 33.4 | 49.6 | 4 | 30.9 | 3.5 | 7.2 |
| 430 | 49.1 | 31.3 | 3.5 | 21 | 3.2 | 6.6 |
| 440 | 75.5 | 21.4 | 4.2 | 13.9 | 3.7 | 5.2 |
| 450 | 112.6 | 18.1 | 5.8 | 9.8 | 5.1 | 3.8 |
| 460 | 153.6 | 21.1 | 8.5 | 8.3 | 7.4 | 2.9 |
| 470 | 184.9 | 29.8 | 12.1 | 9 | 10.4 | 2.3 |
| 480 | 197 | 44.7 | 16 | 11.9 | 13.6 | 2 |
| 490 | 185.2 | 67.3 | 19.2 | 17.5 | 16.4 | 2.1 |
| 500 | 158.4 | 93.6 | 20.4 | 25.9 | 17.4 | 2.4 |
| 510 | 127.5 | 117.8 | 19.4 | 36.2 | 16.5 | 3.1 |
| 520 | 99.4 | 132.8 | 17.1 | 46.6 | 14.5 | 4.2 |
| 530 | 77.6 | 131.3 | 14.3 | 53.1 | 12.1 | 5.7 |
| 540 | 60.6 | 119.5 | 11.6 | 54.3 | 9.8 | 7.1 |
| 550 | 46.8 | 101.1 | 9.3 | 50.7 | 7.9 | 8.3 |
| 560 | 37.4 | 82.6 | 7.5 | 44.1 | 6.4 | 8.7 |
| 570 | 31.2 | 67 | 6.1 | 37 | 5.2 | 8.5 |
| 580 | 27.8 | 53.8 | 5.1 | 30.5 | 4.4 | 7.7 |
| 590 | 27 | 43.1 | 4.3 | 24.8 | 3.7 | 6.7 |
| 600 | 29.2 | 34.8 | 3.8 | 20.2 | 3.3 | 5.8 |
| 610 | 35.2 | 28.3 | 3.7 | 16.5 | 3.2 | 4.9 |
| 620 | 44.9 | 23.8 | 3.7 | 13.7 | 3.3 | 4.2 |
| 630 | 58.6 | 20.7 | 4.1 | 11.6 | 3.6 | 3.6 |
| 640 | 76.1 | 18.4 | 4.8 | 9.8 | 4.2 | 3.1 |
| 650 | 98.5 | 18.5 | 6 | 8.8 | 5.2 | 2.7 |
| 660 | 124.1 | 20.2 | 7.5 | 8.4 | 6.6 | 2.4 |
| 670 | 150.6 | 24 | 9.5 | 8.7 | 8.3 | 2.2 |
| 680 | 175.1 | 29.6 | 11.7 | 9.6 | 10.2 | 2.1 |
| 690 | 194.4 | 37.5 | 14.1 | 11.3 | 12.2 | 2 |

TABLE 2-continued

| 700 | 213 | 47.5 | 17 | 13.7 | 14.6 | | 2.1 |
|---|---|---|---|---|---|---|---|

| WL | 45as60az-54.7 | 45as60az54.7 | 45as75az0 | 45as110az0 | x | y | z |
|---|---|---|---|---|---|---|---|
| 400 | 1.5 | 1.4 | 1.3 | 1 | −0.08 | 5.62 | 24.89 |
| 410 | 1.5 | 1.4 | 1.5 | 1 | −0.04 | 5.09 | 20.55 |
| 420 | 1.3 | 1.3 | 1.7 | 1 | −0.03 | 3.52 | 16.28 |
| 430 | 1.1 | 1.1 | 1.8 | 1 | −0.02 | 1.70 | 14.56 |
| 440 | 0.9 | 0.9 | 1.7 | 1 | −0.03 | −0.13 | 15.82 |
| 450 | 0.8 | 0.8 | 1.5 | 1 | −0.04 | −1.94 | 19.91 |
| 460 | 0.8 | 0.8 | 1.3 | 0.9 | −0.06 | −3.46 | 25.94 |
| 470 | 0.8 | 0.8 | 1.1 | 0.9 | −0.10 | −4.29 | 31.95 |
| 480 | 0.9 | 0.9 | 1 | 0.9 | −0.14 | −4.06 | 36.64 |
| 490 | 1 | 1 | 1 | 0.9 | −0.16 | −2.52 | 39.47 |
| 500 | 1.1 | 1.1 | 1.1 | 0.9 | −0.17 | −0.15 | 40.74 |
| 510 | 1.3 | 1.2 | 1.1 | 0.9 | −0.17 | 2.43 | 40.98 |
| 520 | 1.5 | 1.4 | 1.2 | 0.9 | −0.16 | 4.66 | 40.15 |
| 530 | 1.6 | 1.5 | 1.4 | 0.9 | −0.13 | 5.91 | 37.46 |
| 540 | 1.6 | 1.5 | 1.5 | 0.9 | −0.11 | 6.31 | 33.40 |
| 550 | 1.6 | 1.5 | 1.7 | 0.9 | −0.09 | 6.08 | 28.41 |
| 560 | 1.4 | 1.4 | 1.9 | 0.9 | −0.06 | 5.44 | 23.62 |
| 570 | 1.3 | 1.2 | 1.9 | 0.9 | −0.06 | 4.67 | 19.58 |
| 580 | 1.1 | 1.1 | 1.8 | 0.9 | −0.04 | 3.85 | 16.32 |
| 590 | 1 | 1 | 1.7 | 0.9 | −0.03 | 3.07 | 13.85 |
| 600 | 0.9 | 0.9 | 1.6 | 0.9 | −0.03 | 2.33 | 12.29 |
| 610 | 0.8 | 0.8 | 1.4 | 0.8 | −0.03 | 1.55 | 11.65 |
| 620 | 0.7 | 0.7 | 1.3 | 0.8 | −0.02 | 0.81 | 11.91 |
| 630 | 0.7 | 0.7 | 1.1 | 0.8 | −0.03 | 0.02 | 13.05 |
| 640 | 0.7 | 0.7 | 1 | 0.8 | −0.03 | −0.83 | 14.90 |
| 650 | 0.7 | 0.7 | 1 | 0.8 | −0.05 | −1.70 | 17.93 |
| 660 | 0.7 | 0.7 | 0.9 | 0.8 | −0.05 | −2.59 | 21.73 |
| 670 | 0.7 | 0.7 | 0.9 | 0.8 | −0.07 | −3.38 | 26.12 |
| 680 | 0.8 | 0.8 | 0.9 | 0.9 | −0.08 | −3.97 | 30.62 |
| 690 | 0.8 | 0.8 | 0.9 | 0.9 | −0.11 | −4.28 | 34.88 |
| 700 | 0.9 | 0.9 | 0.9 | 0.9 | −0.14 | −4.42 | 39.54 |

The following Table 3 shows the (x,y,z) coordinates of the measurement directions. Weighting these coordinates by the reflectances at 700 nm in the previous example gives x=17* (−0.42)+14.6*(0.42)+0.9*(−0.71)+0.9*(0.71)=−1.01, and similarly y=−32.94, and z=294.99; dividing by the length of the vector sum of the perfect white reflector (7.46) gives the values shown in Table 2.

TABLE 3

| | 45as-15az0 | 45as15az0 | 45as25az-90 | 45as25az0 | 45as25az90 | 45as45az0 | 45as60az-54.7 | 45as60az54.7 | 45as75az0 | 45as110az0 |
|---|---|---|---|---|---|---|---|---|---|---|
| x | 0.00 | 0.00 | −0.42 | 0.00 | 0.42 | 0.00 | −0.71 | 0.71 | 0.00 | 0.00 |
| y | −0.26 | 0.26 | 0.00 | 0.42 | 0.00 | 0.71 | 0.50 | 0.50 | 0.97 | 0.94 |
| z | 0.97 | 0.97 | 0.91 | 0.91 | 0.91 | 0.71 | 0.50 | 0.50 | 0.26 | −0.34 |

Figure 23:
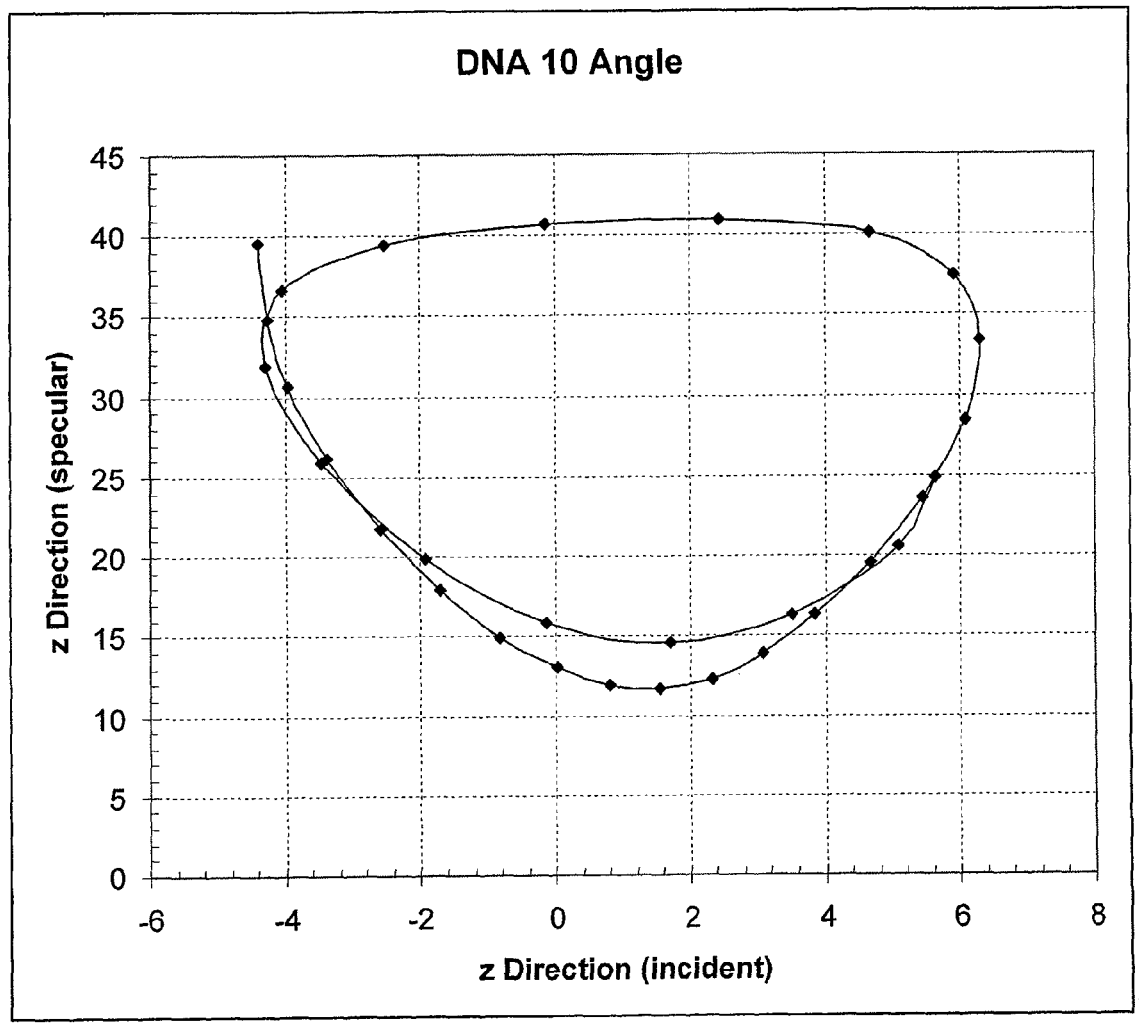
FIG. 23 is an exemplary (y,z) plot of a signature fingerprint for an exemplary surface according to the present disclosure.

A plot of the (y, z) projection based on the DNA coordinates for this hypothetical measured sample, i.e., a fingerprint for such measured sample is set forth in FIG. 23. Of note, any sample/substrate that exhibits the same (or substantially the same) plot will appear identical regardless of lighting, viewing angle, or other environmental conditions. Thus, the disclosed technique and associated systems facilitate matching of color/appearance based on appearance properties, as described herein.

The DNA spectrum disclosed herein incorporates two distinct principles for purposes of measuring, matching or otherwise using/accessing color properties. According to a visual principle, the disclosed DNA spectrum represents the color appearance of the measured surface at a given wavelength. By contrast, according to a structural appearance principle, the unique shape of the DNA spectrum represents the optical properties of the measured surface. In addition, the shape of the DNA spectra can be used to represent, assess and/or determine formulation characteristics. Of note, according to these principles, two samples having DNA spectra of the same shape, but a different position and orientation in space, will have a different color appearance. The difference in position and orientation of their DNA spectra represent process differences.

The disclosed DNA methodology is applicable to any multiangle geometry. The geometry required for measuring a particular class of materials generally depends on the physical properties of the samples to be measured. For example, diffuse materials can be accurately characterized with a single angle measurement. Typically, three positive aspecular angles may be sufficient to characterize coatings with metallic pigments. Adequate measurements of coatings with pearlescent and special effect pigments generally require additional angles beyond the traditional multiangle directions.

There are a number of goals, uses and/or purposes in transforming DNA spectra according to the present disclosure. These goals/uses/purposes include: (i) distinguishing process guiding process changes to compensate for normal variation(s) in coating formulation. As is known in the art, the separation between process and formulation is not entirely sharp. For example, additives such as fumed silica may be used to control metallic flake orientation in a coating. Since the index of refraction of fumed silica matches the index of refraction of common solvents, fumed silica is generally invisible except in its effect on flake orientation. Inasmuch as process variables (e.g., flow rate and atomization) also affect flake orientation, the use of fumed silica is generally not distinguishable from process changes and/or variations.

To determine the equivalence of shapes of DNA spectra, exemplary implementations of the present disclosure employ linear operations of translation, rotation and scaling. With initial reference to the translation operation, translation of a DNA spectrum is based on the average 3D position over all wavelengths. The magnitude of translation may be denoted by xT, and the individual components are therefore denoted xTx, xTy, and xTz. The translation of a DNA spectrum to be centered at the origin is denoted DNAt.

Turning to the rotation operation, the rotation process generally includes three (3) rotations, performed in the following order:
1. A rotation in the xy plane (azimuth)
2. A rotation in the xz plane (colatitude)
3. A rotation in the yz plane (alignment)

The first two rotations are performed so that a best fit plane to the DNA spectrum is rotated to the yz plane. The noted rotations are typically computed based only upon the sample. The pair (azimuth, rotation) is denoted by xR. The rotation of the translated spectrum is denoted DNAt, and the first two rotations are denoted DNAr.

An alignment angle and scale factor are generally computed together using a least squares fit to minimize the distance between a sample DNA spectrum and a standard DNA spectrum. The alignment angle is denoted xA, and the scale factor is denoted xS. Although the alignment angle and the scale factor are computed together, they are generally applied separately. Rotation of the spectrum DNAr in the yz plane by the alignment angle is denoted DNAa, and the result of scaling the spectrum DNAa is denoted DNAs.

In implementing the disclosed systems and methods, care should be taken in determining when to use the aligned spectrum (DNAa) or scaled spectrum (DNAs). In some situations, two samples that differ only in process conditions have significant differences in their aligned spectra DNAa, so examination of the scaled spectra DNAs is needed and/or desired to determine that the difference between samples is indeed a process difference, not a formulation difference.

Of note, the DNA of a surface results from both the underlying material, characterized by DNAs, and its interaction with its environment, represented by application process conditions. In considering DNA transformations, the transformed spectra and the transformation parameters should be considered. In conventional applications, colorimetric values in use with multiangle measurements include Lab values per angle and Flop Index. As is known to persons skilled in the art, Flop Index is a measure of relative lightness change between near specular and near retro angles. The parameters xT, xA, and xS are related to the difference in reflectance at various angles, but they provide different views as compared to a Flop Index.

As an example, in a hypothetical situation a Flop Index of a coating containing metallic flakes can be reduced by coating application under dryer conditions and/or by using finer flakes in the coating. Such changes would more likely be detected by monitoring xT, xA, and xS, as compared to monitoring only the Flop Index. Of course, Flop Index remains a potentially useful tool. For example, multiangle measurements are useful with materials whose multiangle reflectances have multiple dimensions. No single number/parameter can capture all information of interest in such situations.

According to the present disclosure, useful colorimetric data can be advantageously derived from 3D DNA spectra. Among possible approaches to generalizing color difference formulae to higher dimensional spectra include:

1. Computation of colorimetric data, such as XYZ, LAB, and difference formulae on each of x, y, and z planes, and combination of difference formulae computed on the different planes as the square root of the sum of the squares of the single plane difference formulae. The color difference formula computed by generalizing ordinary Delta E may be is denoted dDNA.

2. Computation of XYZ data on each of x, y, and z planes. These values are used as the x,y,z components of vector-valued X, Y, and Z data. The magnitude of the three dimensional X, Y, and Z vectors is then computed, and the L, a, b and color difference data are computed using the one dimensional X, Y, and Z magnitudes.

3. When computing difference formula based on transformed spectra, it is generally advantageous to translate both standard and sample transformed spectra so as to be centered at the center of the standard's DNA spectrum before computing the difference formula. That is, both standard and sample spectra are translated by the standard's (xTx, xTy, xTz) vector. This accounts for the piecewise nature of the CIELAB functions, which are much more sensitive to differences at low reflectance than at high reflectance. The application of Delta E to the various transformed spectra may be denoted dDNAt, dDNAr, dDNAa, and dDNAs.

The application of color difference formula based on human perception may not be desirable or fully effective when considering transformed spectra. Accordingly, in exemplary implementations of the present disclosure, the measure dF, which is calculated as the square root of the sum of the squared distances between corresponding points on the two DNA spectra, is employed. The measure dF thus represents the ordinary Euclidean distance between spectra.

As is known by persons skilled in the art, a logarithmic scale is frequently used instead of a linear scale in reflectance measurements. Accordingly, the measure dG, which involves applying the following non-linear function (8):

$$f(r) = \begin{cases} r^{1/3} & \text{if } r > 0.009 \\ 13.8672 + 7.704r & \text{if } r \leq 0.09 \end{cases} \quad (8)$$

to each reflectance, then applying the dF formula to the result. This function is similar to the non-linear function applied to XYZ values in the CIELAB formula. As with dDNA, dFt, dFr, dFa, dFs, dGt, dGr, dGa, and dGs may be used to denote the result of applying dF or dG to transformed DNA spectra, and plain dF and dG for the result of application to untransformed DNA spectra.

Since the above-noted difference formulae may be applied to untransformed or transformed DNA spectra, it is useful to assess which particular transformation has the greatest effect on the resulting difference formula values. To help in this analysis, the following functions may be used: AdDNA, AdF, and AdG. These functions do not represent a single measure, but any difference of measures. Thus, the AdDNAxy function (where x and y are any of the characters 's', 'a', V, 't', or V appended to DNA) may be used. For example, AdDNAta=dDNAt−dDNAa, and AdGvs=dG−dGs (V is used for untransformed spectra).

To further assist persons of skill in the art in designing and implementing systems, apparatus and methods according to the present disclosure, additional information concerning exemplary quantitative and qualitative information that may be derived and/or computed using, in whole or in part, various statistics and values associated with the disclosed DNA methodology are provided herein below.

DNA Weighted Vector Summation

As noted above, the DNA vector sum is generally a sum of the detector direction vectors, scaled by the reflectance in each direction, as well as an additional weight factor in each direction. The optional weight can be used to restrict the vector sum to certain directions, to emphasize particular directions, and/or to correspond to the energy present in each direction. Often, the specular direction may be excluded from the DNA vector sum (or have an extraordinary scale factor) because the specular channel tends to measure with an extremely high reflectance, but with little color information. Generally, direction measurements and vector sums are generated with a single illuminator, but multiple illuminators may be employed without departing from the spirit or scope of the present disclosure. If data from different illuminators is combined in a single 3D DNA sum, the out-of-plane axes will be aligned. Surface normal vectors and/or specular vectors from the different illuminators' vectors may also be aligned when combining data from different illuminators. Alternatively, data from different illuminators may be combined in a higher dimensional plot because, inter alia, some colors, particularly those with strong interference pigments, have multiangle data that is effectively more than three dimensional, so that a 3D DNA sum would potentially lose valuable information. Of note, if the detector directions are all in-plane, the DNA sum will lie in a two-dimensional space.

To derive an exemplary DNA fingerprint in three dimensional space according to the present disclosure, equation (9) may be used:

$$DNA_\lambda = \sum_\mu R_{\lambda,\mu} \cdot w_\mu \cdot (\mu_x, \mu_y, \mu_z) \tag{9}$$

where R is the 31×m matrix of measured reflectance values (for 31 wavelength measurements), $R_\lambda$ is the reflectance at wavelength $\lambda$ and measurement direction $\mu$, $\mu_x$, $\mu_y$, and $\mu_z$ are the components of the measurement direction, where the z, y, and x components are the specular direction, the in-plane projection of the illuminator direction orthogonal to specular, and the out-of-plane direction, respectively, and $W_\mu$ is the additional weight in direction p.

The translation vector for a DNA curve is the sum over wavelengths of the DNA. This gives a translation vector $$(xTx, xTy, xTz) = \sum_\lambda DNA_\lambda$$

n 3D space. The translated DNA is DNAt=DNA−(xTx, xTy, xTz), and the norm of the translation vector is $xT = \sqrt{xTx^2+xTy^2+xTz^2}$.

The alignment of DNA curves is generally performed in two steps. First, the rotation angles are computed to align the best fit plane to the DNA curve with the yz-plane. These angles are the azimuth and colatitude. The second step is to simultaneously compute a rotation angle within the yz plane and a scale factor using least squares.

To minimize numerical instability in computing the best fit plane, it may be desirable to shift the DNAt curve away from the origin. The result of such shift may be called M, which may be computed with formula (10):

$$M=DNAt+(10,0,0). \tag{10}$$

The best fit plane to M satisfies an equation of the form $\vec{x} \cdot \vec{n} = k$, where $\vec{n}$ is the normal vector to the plane and k is a constant. Since M does not go through the origin, k is non-zero. Thus, M satisfies an equation of the form $M\vec{n} = k\vec{v}$, where $\vec{v} = [1\ 1\ \ldots\ 1]^T$. The normal vector n may then be computed to the best fit plane as the least squares solution to the foregoing equation; using the normal equations approach. The solution is based on the equation $M^T M \vec{n} = M^T \vec{v}$. Thereafter, $\vec{n}$ may be scaled so that it is a unit vector.

To compute the azimuth and colatitude from the normal vector, the following equations may be used:

$$\text{Azimuth} = \arctan 2(n_y, n_x) \tag{11}$$

$$\text{Colatitude} = \arctan 2(n_z, \sqrt{n_x^2+n_y^2}) \tag{12}$$

The result of rotating DNAt by the azimuth and colatitude may be denoted DNAr. For an azimuth of $\alpha$ and colatitude of y, the rotated curve may be computed as:

$$DNAr = DNAt \begin{bmatrix} \cos(\alpha) & \sin(\alpha) & 0 \\ -\sin(\alpha) & \cos(\alpha) & 0 \\ 0 & 0 & 1 \end{bmatrix} \begin{bmatrix} \cos(\gamma) & 0 & \sin(\gamma) \\ 0 & 1 & 0 \\ -\sin(\gamma) & 0 & \cos(\gamma) \end{bmatrix} \tag{13}$$

The in-plane alignment angle and scale factor are computed with reference to a standard. For a given DNAr curve, form the matrix $$P = \begin{bmatrix} DNAr_y & DNAr_z & J & Z \\ -DNAr_z & DNAr_y & Z & J \end{bmatrix},$$

where $DNAr_y$ and $DNAr_z$ are 31×1 vectors containing the y and z components of DNAr, respectively; J is the 31×1 vector of all 1's; and Z is the 31×1 vector of all 0's. The linear system $P_{sample}X = P_{standard}$ may then be solved to yield an in-plane alignment angle, which is $xA = \arctan 2(-X_{2,1}, -X_{1,1})$, and the scale factor is $xS = \sqrt{X_{1,1}^2 + X_{2,1}^2}$. The aligned DNA is $$DNAa = DNAr \begin{bmatrix} 1 & 0 & 0 \\ 0 & \cos(xA) & \sin(xA) \\ 0 & -\sin(xA) & \cos(xA) \end{bmatrix},$$

and the scaled DNA is DNAs=xS·DNA.

Figure 27:
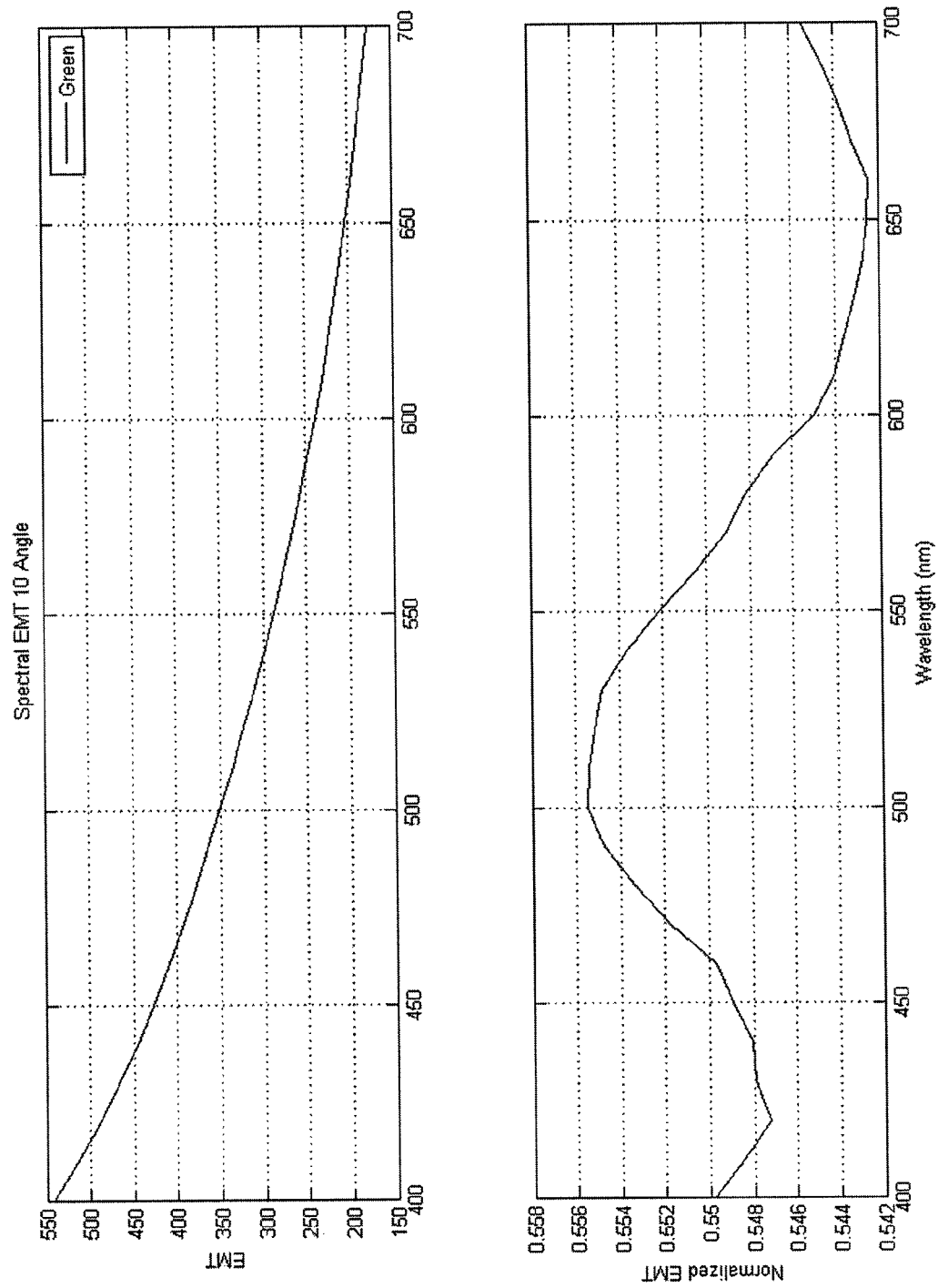
FIG. 27 shows an EMT curve for a homogeneous material.
Figure 28:
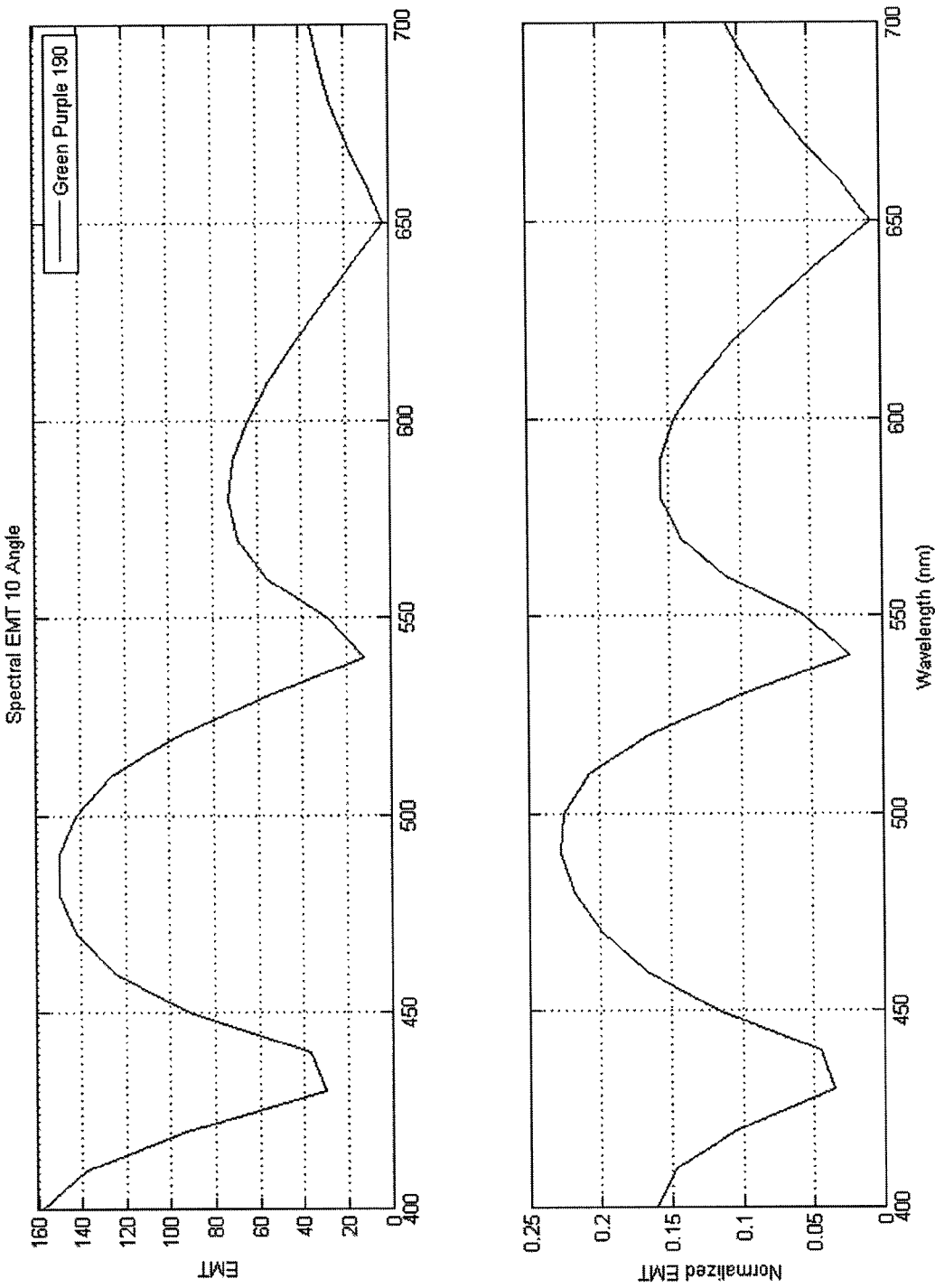
FIG. 28 shows an EMT curve for a Chromaflair™ dielectric flake material (Flex Products) showing impedance mismatches.

EMT is the relative power in the xy components of the DNA curve. Graphically, this may be presented directly, or weighted by the inverse wavelength squared to mimic a dispersion curve. FIG. 27 shows a representative EMT curve for a homogeneous material and FIG. 28 shows an EMT curve for Chromoflair™ dielectric flake material (Flex Products) showing impedance mismatches. If EMT refers to the weighted version, the unweighted version may be denoted by EMTn. The equations for computing such EMT values are:

$$EMTn_\lambda = \frac{\sqrt{DNA_{\lambda,x}^2 + DNA_{\lambda,y}^2}}{\sqrt{DNA_{\lambda,x}^2 + DNA_{\lambda,y}^2 + DNA_{\lambda,z}^2}} \quad (14)$$

$$EMT_\lambda = \frac{16\pi^2 EMTn_\lambda}{\lambda^2} \quad (15)$$

CIELAB, DE and DE94 values may be computed on each plane of the DNA curve, and then the planes may be combined to arrive at single L, a, b, and/or DE values based on the DNA curve. The single DE values may be denoted dDNA and such values may be computed on raw or transformed DNA curves. Delta dDNA values may also be computed based on the difference of different transformed dDNA values.

The first step in computing CIELAB data is generally to compute XYZ values based on a specified illuminant and a specified observer. In the case of 31 point data, this computation involves multiplication of a 3×31 weight matrix by a 31×1 vector to produce a 3×1 vector. The corresponding step when the spectral data is a DNA curve in 3-dimensional space is to multiply the weight matrix by the DNA curve, arranged as a 31×3 matrix, as shown in equation (16):

$$\begin{bmatrix} x_\lambda \\ y_\lambda \\ z_\lambda \end{bmatrix} \cdot DNA = \begin{bmatrix} X_x & X_y & X_z \\ Y_x & Y_y & Y_z \\ Z_x & Z_y & Z_z \end{bmatrix} \quad (16)$$

The CIELAB functions may then be applied to the XYZ data of each column individually:

$$\begin{bmatrix} L_x & L_y & L_z \\ a_x & a_y & a_z \\ b_x & b_y & b_z \end{bmatrix} = \quad (17)$$

$$\begin{bmatrix} CIE\_L(X_x, Y_x, Z_x) & CIE\_L(X_y, Y_y, Z_y) & CIE\_L(X_z, Y_z, Z_z) \\ CIE\_a(X_x, Y_x, Z_x) & CIE\_a(X_y, Y_y, Z_y) & CIE\_a(X_z, Y_z, Z_z) \\ CIE\_b(X_x, Y_x, Z_x) & CIE\_b(X_y, Y_y, Z_y) & CIE\_b(X_z, Y_z, Z_z) \end{bmatrix}$$

To compute dDNA between two measurements, the square root of the sum of the squares of the differences between the 3×3 vectors is computed according to equation (18):

$$dDNA = \sqrt{\begin{array}{l}(L_x - L'_x)^2 + (a_x - a'_x)^2 + (b_x - b'_x)^2 + \\ (L_y - L'_y)^2 + \ldots + (a_z - a'_z)^2 + (b_z - b'_z)^2\end{array}} \quad (18)$$

The DNA curve utilized in the above-noted computations may be the raw DNA curve, or one of the transformed curves DNAt, DNAr, DNAa, or DNAs. It is noted that dDNAt, dDNAr, dDNAa, and dDNAs are generally used for the results of computing dDNA on transformed curves.

For purposes of calculating DF, DG, Delta DF and Delta DG, the square root of the sum of squared differences of reflectance on DNA curves may be computed, without the perceptual weighting of CIELAB, giving:

$$DF = \sqrt{\begin{array}{l}\sum_\lambda (DNA_{\lambda,x} - DNA'_{\lambda,x})^2 + \\ (DNA_{\lambda,y} - DNA'_{\lambda,y})^2 + (DNA_{\lambda,z} - DNA'_{\lambda,z})^2\end{array}} \quad (19)$$

The noted values may also be computed on raw and transformed DNA curves, giving DFt, DFr, DFa, and DFs. If the non-linear function $$f(r) = \begin{cases} r^{1/3} & \text{if } r > 0.009 \\ 13.8672 + 7.704r & \text{if } r \leq 0.09 \end{cases}$$

is first applied to reflectance values, equation (20) results:

$$DG = \sqrt{\begin{array}{l}\sum_\lambda (f(DNA_{\lambda,x}) - f(DNA'_{\lambda,x}))^2 + \\ (f(DNA_{\lambda,y}) - f(DNA'_{\lambda,y}))^2 + (f(DNA_{\lambda,z}) - f(DNA'_{\lambda,z}))^2\end{array}} \quad (20)$$

and DGt, DGr, DGa, and DGs may be used to denote the values computed from transformed curves.

The traditional DE, DE94 and DEp/DIN6175-2 formulae may be applied to each angle individually. It is noted that the aspecular angle is required for DIN 6175-2, and the absolute value of the designated aspecular angle (i.e., 15 for the −15 direction) may be used. The Flop Index is typically computed in a traditional manner using 15°, 45°, and 110° L values.

Figure 24:
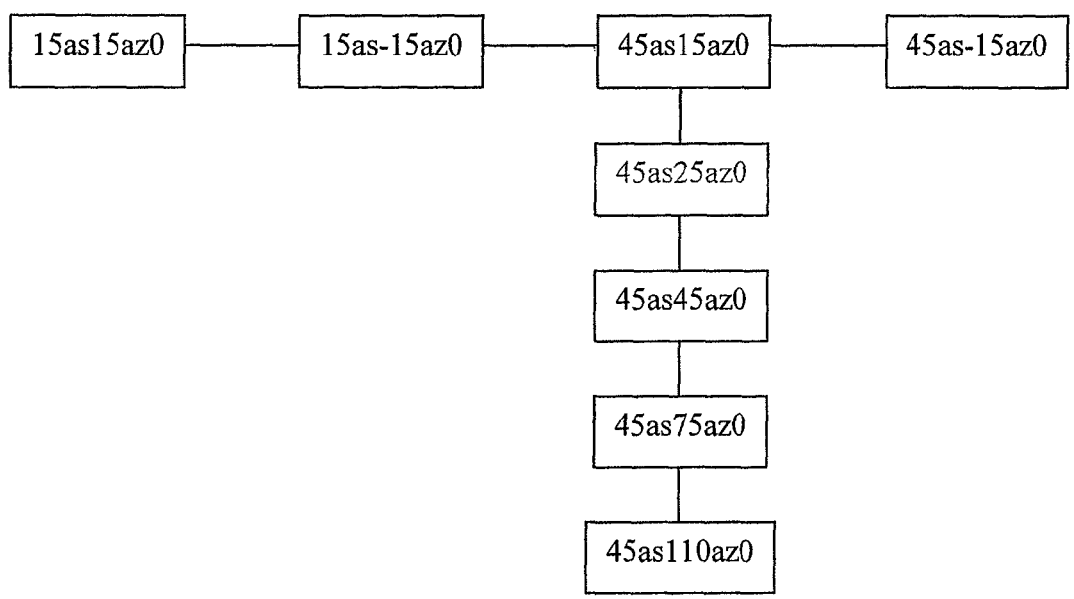
FIG. 24 is a chromaticity plot of per-angle value pairs showing the aspecular line and a rough approximation of the interference line for a surface according to the present disclosure.

As shown in FIG. 24, the per-angle (a*, b*) value pairs may be plotted for the 45° illuminator directions, and for the 15° illuminator, ±15° aspecular directions. The value pairs are connected in a T shape, showing the aspecular line and a rough approximation of the interference line.

For purposes of the discussion which follows, the term "DNA" is replaced by the term "xDNA". However, with reference to Formula (9) set forth herein above and like "DNA", "xDNA" is also defined as:

$$xDNA_\lambda = \sum_\mu R_{\lambda,\mu} \cdot w_\mu \cdot (\mu_x, \mu_y, \mu_z) \quad (21)$$

It is noted that the specular direction will often be excluded from this sum, or have an extraordinary scale factor related to the dielectric constant of the material and air (or the medium in which it is measured), as the specular channel tends to measure with an extremely high reflectance, but with little color information. It is generally expected that vector sums will include directions measured with just one illuminator. Among the numerous possible ways to combine data from multiple illuminators in a single xDNA sum, two exemplary options are presented herein:

Plus-specular Align the specular directions (z-axis), projection of illumination directions (y-axis), and out-of-plane directions (x-axis) from the 45° and 15° xDNA curves. Compute the average vector sum of the two xDNA curves in this coordinate system.

Times-normal Align the sample normal directions, projection onto sample plane of illumination directions (y-axis), and out-of-plane directions (x-axis) from the 45° and 15° xDNA curves. Compute the product of the two xDNA curves in this coordinate system, and divide by 100.

It may be that a combination of data from different illuminators in a higher dimensional plot is desired. The reason for this may be that the some colors, particularly those with strong interference pigments, have multiangle data that is effectively more than three dimensional, so that a three dimensional xDNA sum loses too much information. Note that if the detector directions are all in-plane, the xDNA sum lies in a two-dimensional space.

As noted above, for some coatings and materials, change(s) due to process can be separated from material makeup (over limited ranges) by rotations and translations, and change(s) due to batch distribution and concentration can be separated by scaling. For this purpose, an algorithm may be employed, e.g., the Procrustes algorithm or other such approach, to rotate, translate and scale two results for comparison purposes.

Through use of the Procrustes algorithm for finding spatial transformations of xDNA spectra, for a given sample and standard, the algorithm produces a 3×1 translation vector, a 3×3 rotation matrix, and a scale factor. A transformed xDNA spectra may be obtained by applying the resulting parameters, and then translating the sample to have the same center as the standard. A reason for the extra translation in the xDNA spectra is to better account for the effect of a given step on xDNA shape difference. Individual outputs of the Procrustes algorithm are computed in the context of later steps, so that using them directly may artificially increase shape difference. Nonetheless, it may be desired to use individual outputs directly in the xT, xA, and xS statistics, as otherwise the extra translation will have an excessive influence on the correlation of these statistics across samples.

Thus, in an exemplary implementation of the Procrustes Algorithm: Let A be a sample xDNA spectra, and let B be a standard xDNA spectra. The parameters of a transformation of A may be computed that gives the best match to B. Represent A and B as p×k matrices, where p is the number of wavelengths and k is the number of spatial dimension. Let J be the p×1 matrix with every entry equal to one. Let $I_p$ be the p×p identity matrix. Define the matrix S by:

$$S = A^T \left( I_p - \frac{JJ^T}{p} \right) B. \tag{22}$$

Now, to compute the eigenvectors of $SS^T$ and $S^TS$, let v be the matrix whose columns are the eigenvectors of SST, and let w be the matrix whose columns are the eigenvectors of $S^TS$, and defining the rotation matrix Rot by Rot=vw$^T$.

It is noted that permuting the columns of the eigenvector matrix will give another eigenvector matrix. The eigenvectors of v and w must be ordered consistently. For example, the MATLAB function 'eig' returns the eigenvectors in order of increasing eigenvalue. For the typical situation, when the sample and standard are similar colors, the rotation matrix should end up close to the identity matrix. If x is an eigenvector, then so is −x. It is necessary to ensure that the largest component (in absolute value) of each eigenvector x is positive; if not, replace x with −x.

Define the scale factor by Scale=trace(Rot$^T$S)/trace $$\left( A^T \left( I_p - \frac{JJ^T}{p} \right) A \right).$$

Define the translation vector by $$Trans = \frac{J^T}{p} \left( \frac{BRot^T}{p} - A \right).$$

The output of the Procrustes algorithm is the 3×1 translation vector Trans, the 3×3 rotation matrix Rot, and the scale factor Scale.

The translation vector for an xDNA curve is given by $$xT = \sum_{m=1}^{3} Trans(m)^2,$$

and the following may be used: xTx=Trans(1), xTy=Trans(2), and xTz=Trans(3). The translated xDNA is $$xDNAt = \left( I_p - \frac{JJ^T}{p} \right)(A + JTrans) + \frac{JJ^T}{p} B.$$

The rotation that results from the Procrustes algorithm with Euler angles. The alignment angle may be defined as xA=arctan 2(−Rot(3,2),Rot(3,3)), and the azimuth and co-latitude components of xR may be defined by xR.azimuth=arctan 2(−Rot(2,1),Rot(1,1), and xR.colatitude=arcsin(−Rot(3,1)).

The application of the rotation matrix to the xDNA spectrum gives the aligned xDNA:

$$xDNAa = \left( I_p - \frac{JJ^T}{p} \right)(A + JTrans)Rot + \frac{JJ^T}{p} B. \tag{23}$$

The scale factor resulting from the Procrustes algorithm may be denoted by xS=Scale. The scaled xDNA may be computed as xDNAs=(A+J Trans)Rot Scale. It is noted that the extra factor $$\left( I_p - \frac{JJ^T}{p} \right)$$

and extra term $$\frac{JJ^T}{p} B$$

are not needed in this expression, as applying all parameters from the Procrustes algorithm automatically results in the standard and transformed sample having the same center.

Because this approach preserves the dispersive nature of the material, it is possible to create a normalized result that is proportional to the dispersion of the refractive index of the material, as denoted by EMT (see FIGS. 227 and 28).

From these examples of computing tristimulus results from xDNA results, it is readily apparent that unique metrics (that are not perceptually weighted) may be developed that can be computed from the xDNA results and that provide direct process and formulation characteristics and/or tolerances.

For example, in an automotive coating, the similarities associated with mica flakes and Xirallic flakes (EMD Chemicals Inc.) will be effectively distinguished because the two flake materials will impart uniquely different signatures in xDNA space. Accordingly and advantageously, the presence and/or classification of such materials, e.g., due to mean size distribution and/or concentration is possible. Indeed, a method is provided for relating change(s) in process, formulation, distribution and/or recipe, to visual perceptual changes for desired purposes, e.g., for formulation development and/or visualization on a computer screen.

Using the computational methods above, the present disclosure provides an advantageous and powerful way of coupling perceptual visual metrics with formulaic measured and predicted results. By developing merit functions and weightings based on these metrics and combining them with optimization algorithms, it is possible to create new formulations, develop batch corrections to bring formulations and processes back within perceptual tolerance limits, and to develop and drive new visualization computer graphic shader models based on various xDNA parameters and metrics.

Many different optimization algorithms exist and can be used in connection with the disclosed systems/methods, e.g., Levenberg-Marquardt, Golden Section, Damped Least Squares, genetic, micro genetic, Fuzzy and the like. The basics steps of such optimization algorithms are generally iterative, with a goal of converging to a solution that minimizes (or maximizes) some function. In exemplary embodiments of the present disclosure, an optimization algorithm may be employed to derive/converge to a function that is derived from xDNA parameters. Furthermore, improvements to computer visualization may be made by driving shader models based on xDNA parameters and their results, such as identification of materials, classification of material characteristics by size, shape, concentration, process and batch difference. By combining conventional models of recipe formulation with models for material and coating process application, xDNA, and with computer visualization, it is possible to provide a unique advanced solution for both accurate visualization of color and appearance, along with a more rigorous formulation, batch correction and production quality control tool.

Figure 25:
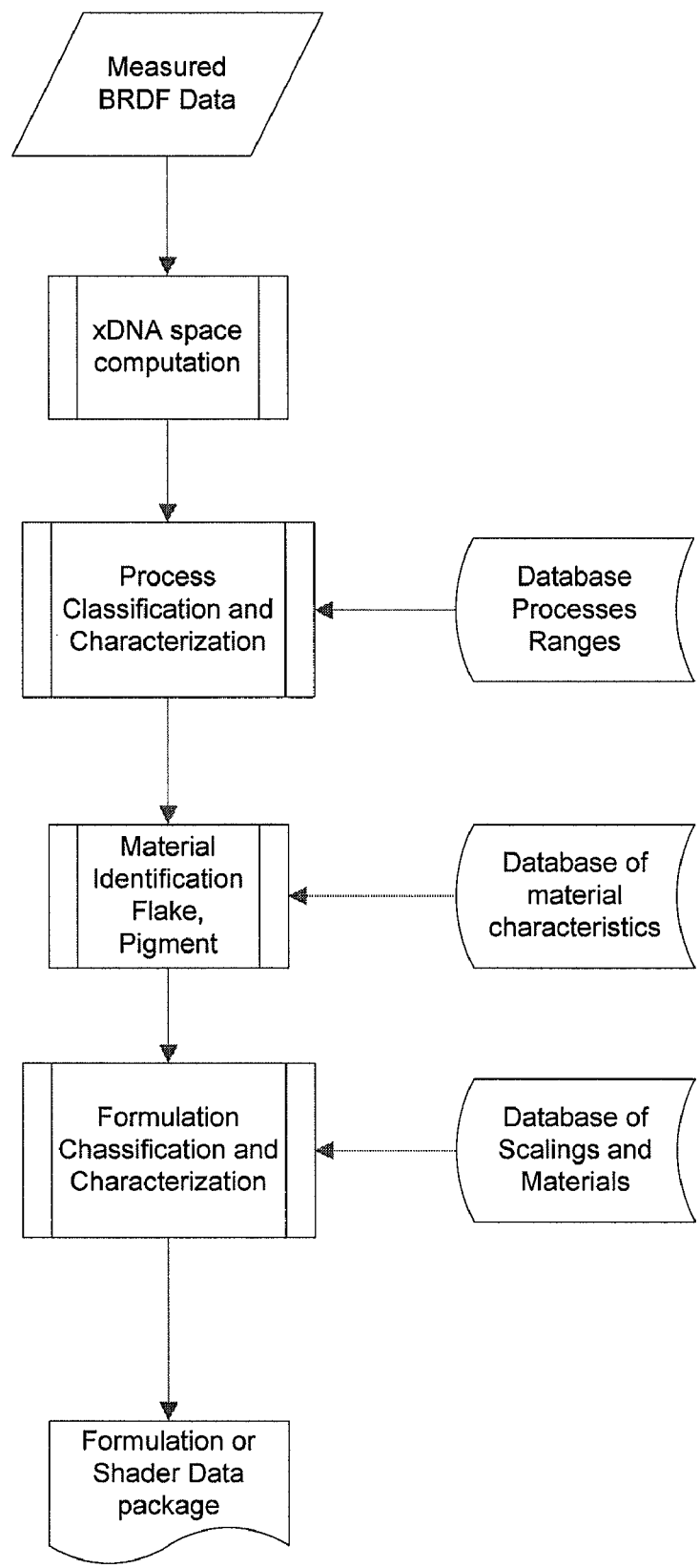
FIG. 25 shows a representative flow chart of a method for processing measurement or defined color appearance into a processed data package.

With reference to FIG. 25, an exemplary flow chart for implementing the disclosed methods/systems is provided. Thus, as a first step, BRDF data (or other data of comparable type/character) is obtained for a desired object/surface. A vector sum of the first reflectance direction, the second reflectance direction and the third reflectance direction over a plurality of wavelengths are plotted on a three-dimensional surface to create a three dimensional curve to describe the color of the object, such three dimensional curve being termed the xDNA space computation for such object/surface. The disclosed system/method then accesses one or more databases containing xDNA for one or more of the following: known processes, known material characteristics and/or known formulations. As shown in FIG. 25, the disclosed process may entail accessing database information with respect to each of the noted parameters, but the present disclosure further contemplates accessing less than each of the noted databases, as may be appropriate for a given undertaking or system/process implementation.

Based on the data contained in the noted databases, which contain xDNA for known conditions/materials/parameters, and a comparison of such known or reference xDNA values, the disclosed system/method is effective in (i) process classification and characterization for the object/surface of interest, (ii) material identification (e.g., flake, pigment, etc.) for the object/surface of interest, and (iii) formulation classification and characterization for the object/surface of interest. Based on the foregoing classification/identification steps, the disclosed system/method is adapted to generate a formulation and/or shader data package that can be advantageously employed to predict a formulation, yield a more accurate formulation recipe or visualization model, and/or render the color of an object/surface on a visual display unit, e.g., a computer graphics display/monitor.

Figure 26:
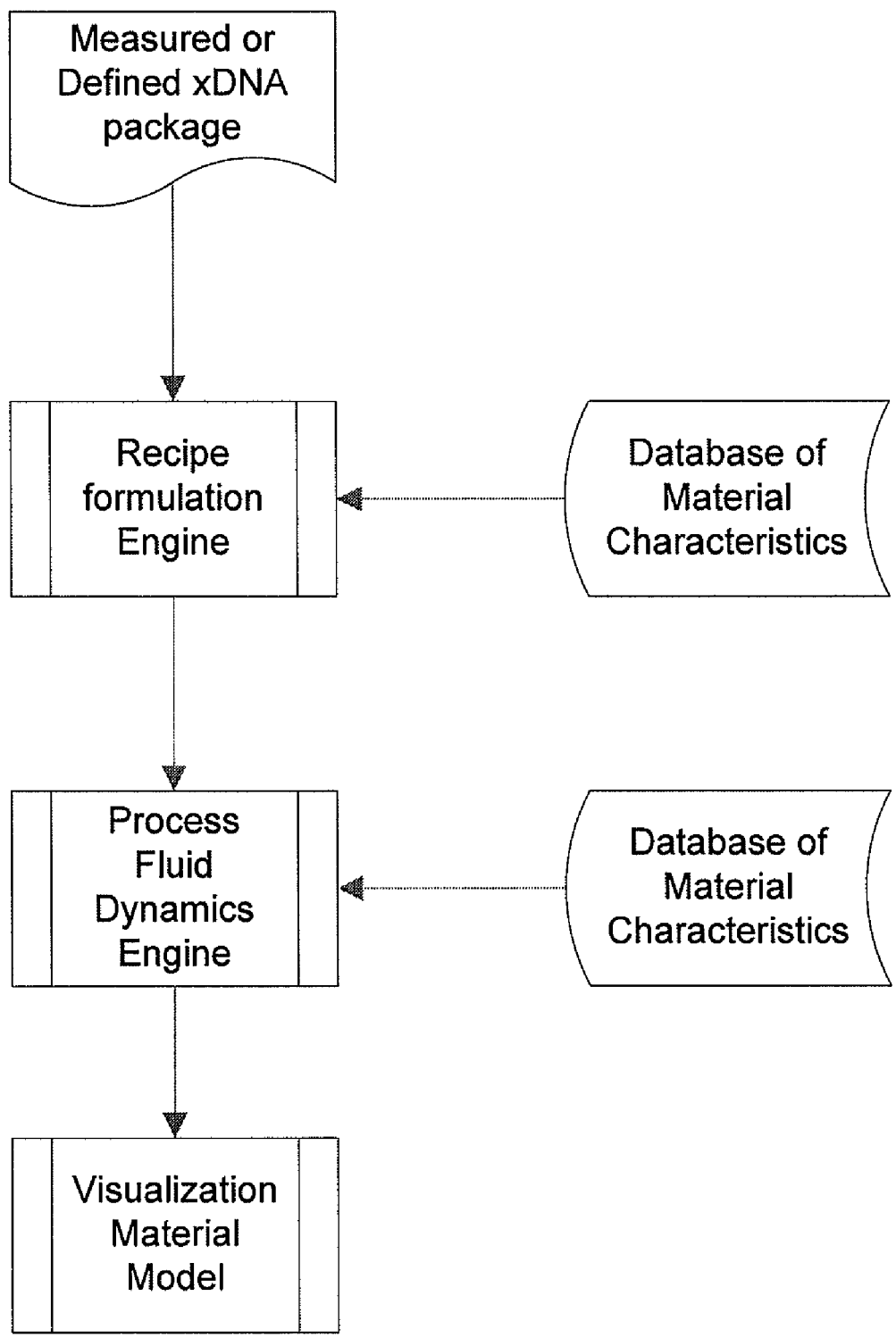
FIG. 26 shows a representative flow chart for processing xDNA data package(s) for development of a recipe formulation and visualization.

FIG. 26 provides a flow chart of an alternative implementation of the present disclosure, wherein a measured or defined xDNA package runs through a "recipe formulation engine" (in which, for example, a database of known/reference material characteristics is accessed and compared) and a "process fluids dynamic engine" (in which, for example, a database of known/reference material characteristic is accessed and compared). Based on the flow chart schematically depicted in FIG. 26, a visualization material model is advantageously generated.

Thus, as is apparent from FIG. 26 and the totality of the present disclosure, in addition to conventional formulation and optimization algorithms described above, it is possible to also include and implement conventional processing models, such as fluid dynamics, computational fluid dynamics, aerosol models, etc., according to the present disclosure. Additionally, the disclosed systems and methods may be applied to conventional rendering and rasterization shaders, as well as Ray Trace based shader models. Although current display technologies are 8 and 10 bit RGB in nature, it should be readily apparent that the benefits of a full spectral solution that seamlessly connects the formulation and process models with more rigorous shader and visualization systems is achievable according to the present disclosure.

To further illustrate advantages and wide ranging applicability of the disclosed systems, apparatus and methods, reference is made to the following exemplary "use case scenarios." The present disclosure is neither limited by nor to the exemplary scenarios described herein. Rather, the exemplary "use case scenarios" presented herein are by way of example, and not limitation. For purposes of these exemplary "use case scenarios", the referenced DNA may be read and understood as equivalent to xDNA and may be used in the further processing as disclosed, for example, in FIGS. 25 and 26. As will be readily apparent to persons skilled in the art, the disclosed systems, apparatus and methods may be used and/or implemented in many alternative ways and environments.

Exemplary Use Case Scenario #1

An automobile manufacturer and a paint supplier desire to coordinate and collaborate in the development, selection and implementation of one or more paint formulations. The paint supplier formulates a palette of colors and effects for review by the automobile manufacturer. In a preferred collaboration methodology, the color palette is developed using color formulation software provided by X-Rite, Inc., the assignee of the present application, and the manufacturer and supplier exchange physical samples and electronic data to facilitate the collaborative effort. Electronic data is advantageously facilitated with visual appearance management software/solutions, e.g., monitor optimizers and/or auto software.

Based on the manufacturer's selection(s), the supplier develops production recipes and processes using robotic spray booths. A series of panels are then sprayed to create a design of experiment (DOE) around formulation and process variations in order to establish baseline tolerances for full appearance. DNA prints are created for each panel and the expression values computed for each variant relative to the sample selected by the manufacturer. Recipe variants are tested based on variations of pigment grind, e.g., based on grind samples at 50% of the original, 75% of the original, and over grind.

These expression values are used to establish baseline tolerances for DNA distortion (e.g., formulation and lot to lot variation) and expression (e.g., process flow/atomization) magnitudes by interpolating the BRDF patterns between the original sample and the variants. Using the DNA results from the variant study, the minimum perceptual limit and acceptable perceptual production limits for all illumination/observation conditions are determined.

The formulation may then be released by the supplier for production and a final run of panels, e.g., 1000 panels. The panels are graded and sorted to create the QA masters for use at various manufacturing and supply-related locations, and for in-house supplier use. DNA prints are automatically computed for each plate and sorted by process around the desired DNA centroid. A virtual standard centroid and tolerances for each print group are also created for distribution with the master plates. Of note, the DNA prints represent all possible viewing conditions, i.e., total appearance, thereby ensuring accuracy.

Colorimetric values and DNA's are created from the collected measurements and used to compare to the samples provided to the manufacturer. Once the baseline recipe, process, and formulation are released for production, the process of transferring to others involved in the manufacturing process may commence. For example, the automobile manufacturer may receive the DNA files from the supplier and import them into a software system. The DNA database immediately provides a master fingerprint along with a 3D set of tolerances that would help guide the manufacturer and its QC team to implement production.

Exemplary Use Case Scenario #2

An automobile manufacturer has been engaged in production for a period of time, e.g., three (3) months. A manufacturing location desires to ensure that the color appearance of its automobiles matches the master standard in all respects, e.g., regardless of lighting and/or viewing angle. DNA tolerances according to the present disclosure are used to monitor production. Standards and tolerances are established for production line(s) and, using a portable color measuring apparatus according to the present disclosure, manufacturing personnel are able to track the DNA process, formulation, and recipe expression tolerances, as well as the change in those tolerances (dF, dFb, dFg, dFr). Colorimetric measurement may only be necessary when the process drift indicator signals an out-of-tolerance condition. Because manufacturing personnel can directly relate the process tolerances to the nominal condition, process parameters may be adjusted based on the new tolerance statistics directly.

In the event a measurement indicates that the dF tolerances are out of range, the systems, apparatus and method of the present disclosure facilitate prompt and efficient troubleshooting and corrective action. For example, by comparing the measurement results to the process standard, manufacturing personnel may determine that a low atomization/low flow condition exists. In response, an adjustment to the flow and atomization settings may be made and confirmatory measurements taken. A series of iterations may be necessary to achieve an appropriate settings.

Because each paint system has a unique "DNA" represented by the points plotted in 3D space and that pattern is dependent on the recipe for the paint and the process settings used, corrective action is facilitated according to the present disclosure. The closer the two DNA's for two samples are, the closer they will appear under all viewing conditions. If something changes, the DNA would move in space and/or change shape. By determining how much the DNA's change over time (e.g., with tracking reports) and whether the change is in shape, position or both, it is possible to determine the cause of the problem. Indeed, exemplary instruments of the present disclosure can overlay and scale the measurements for analysis and corrective action. For example, it may become apparent ~ after scaling << that it was the same paint coating, and that therefore the production line issue must have been caused by a process change.

Exemplary Use Case Scenario #3

After a period of manufacture, it is noted that measurements indicate something has changed with respect to the body paint. Although the color looks correct, the measurements indicate the line is now running at the limit of the allowable tolerances. The issue is not yet visually perceivable but, if the process is allowed to continue to drift, the color issue will become visually apparent. Manufacturing personnel are confronted with a need to diagnose the problem, e.g., to determine if the issue may have been caused by the paint spray equipment, a new batch of paint, or some other issue. In troubleshooting the issue, measurements are taken of multiple body part locations, e.g., the fenders and the hood.

Once the data is collected, the manufacturing personnel advantageously view the DNA shapes and check the xA plots and xS plots. The xS plots look identical to the master standard, so they are confident the paint formulation has not changed. However, the xA may be a different size relative to the Master Panel data. On this basis, the manufacturing personnel may decide to compare the dF's for the hood and door panels to the Master sample data. If they look different, the Delta dF's may be plotted, which might show that the hood is in fact different as compared to the door, even though they are sprayed at the same time. This phenomenon may suggest that the particle size has changed, e.g., due to larger/heavier flakes falling out of the droplet cloud and not making it to the vertical sides of the automobile body. Of note, if only the process had varied, the Delta dF's for the hood and door panel would have been similar.

These types of issues may be caused by under-grinding or over-grinding of pigment, or an incorrect flake size, e.g., due to settling. Sampling of the incoming lot of flakes is not always representative of how an entire lot will behave. A panel study on the pigment may be helpful in diagnosing the problem, e.g., to determine if the process may have been impacted by changes in humidity and temperature. A panel study generally involves grinding the current lot of pigment to various levels from under grind to over grind. The panels can then be compared, inter alia, to the original master panel study. For example, the over ground results of the panel study may match up with the master panel study, suggesting that humidity is the issue. Corrective action may involve a shortening of the grinding cycle for the next lot of material.

According to the above-noted implementation of the disclosed system/method, corrective action is possible before the process is out of control and/or before someone notices a visual difference. Absent early corrective action, production vehicles would likely have been processed with a color variant beyond acceptable tolerances.

Exemplary Use Case Scenario #4

A bumper manufacturer (OEM) for an automobile manufacturer receives the master panels and associated DNA database for a new bumper from the manufacturer. A sample lot is provided for the OEM's use in manufacturing the bumpers. To permit sourcing of the underlying paint from multiple sources (or from an alternative source relative to the developer of the relevant paint), a process study is completed to understand the paint formulation. Based on the measurement results, the OEM determines that a reasonable match can be achieved, but by comparing the DNA prints, the dF's, and the dDNA's, it is apparent that the current formulation and the new formulation are different, requiring the OEM to hold tighter process tolerances to allow for lot to lot variations in paint, while not resulting in a difference in appearance under certain lighting conditions.

Based on the results of the process study, the OEM uses the xA values to establish a virtual process centroid for the formulation. According to the present disclosure, the OEM is able to compare first master panel values to those from the process study and immediately identify the closest samples. Using the DNA results, the disclosed software/system estimates the "ideal" xA values for the DNA that would provide the best match to the master and the largest tolerances. The OEM may use the differences in process settings and their associated xA values to estimate the ideal process settings. Using baseline process settings, the OEM can prepare sprayed samples for measurement. Based on the reasonably close match in DNA and, after colorimetric confirmation checks, the OEM is able to move forward with OEM manufacture of the new bumper.

It is to be understood that the figures and descriptions of the present invention have been simplified to illustrate elements that are relevant for a clear understanding of the present invention, while eliminating, for purposes of clarity, other elements, such as, for example, some specific tasks of the non-execution service provider units described above, etc. Those of ordinary skill in the art will recognize that these and other elements may be desirable. However, because such elements are well known in the art and because they do not facilitate a better understanding of the present invention, a discussion of such elements is not provided herein.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for processing data for standalone application and/or over a networked medium or media. Computers and computer systems disclosed herein may include operatively associated memory for storing certain software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, ROM (read only memory), RAM (random access memory), PROM (programmable ROM), EEPROM (extended erasable PROM), and/or other like computer-readable media.

The various modules 916, 918 of the system 901 may be implemented as software code to be executed by a processor(s) of the system 901 or any other computer system using any type of suitable computer instruction type. The software code may be stored as a series of instructions or commands on a computer readable medium. The term "computer-readable medium" as used herein may include, for example, magnetic and optical memory devices such as diskettes, compact discs of both read-only and writeable varieties, optical disk drives, and hard disk drives. A computer-readable medium may also include memory storage that can be physical, virtual, permanent, temporary, semi-permanent and/or semi-temporary. A computer-readable medium may further include one or more data signals transmitted on one or more carrier waves.

While several embodiments of the invention have been described, it should be apparent that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

We claim:

1. A method for formulating or rendering of a surface, comprising:
    illuminating the surface with a first light source incident on the surface from a first illumination direction at a plurality of wavelengths;
    measuring reflected light at the plurality of wavelengths in a plurality of reflectance directions, wherein the plurality of reflectance directions includes at least a first reflectance direction, a second reflectance direction and a third reflectance direction;
    calculating an xDNA for the surface based on the measured reflected light, wherein the xDNA defines a weighted directional response of the surface that includes a set of vectors, and wherein each vector of the set of vectors represents a vector sum of light measured over all of the plurality of reflectance directions at a given wavelength or wavelength range; and
    using the xDNA to generate a color formulation or to render the surface on a display device.

2. A method according to claim 1, wherein the measured reflected light comprise Bidirectional Reflectance Distribution Function (BRDF) data.

3. A method according to claim 1, wherein the xDNA is calculated according to the following formula:

$$xDNA_\lambda = \sum_\mu R_{\lambda,\mu} \cdot w_\mu \cdot (\mu_x, \mu_y, \mu_z).$$

4. A method according to claim 1, wherein use of the xDNA to generate a color formulation or to render the surface on a display device includes at least one of:
    (a) accessing at least one database that contains known or reference process ranges and comparing the xDNA with the known or reference process ranges to determine a process classification;
    (b) accessing at least one database that contains known or reference material characteristics and comparing the xDNA with the known or reference material characteristics to determine a material identification; and
    (c) accessing at least one database that contains known or reference materials and comparing the xDNA with the known or reference materials to determine a formulation classification.

5. A method according to claim 4, wherein at least one of the process classification, material identification and formulation classification is used to calculate a shader data package for the surface being rendered.

6. A method according to claim 5, further comprising evaluating an estimated color of the rendered surface by:
    rendering the estimated color of the surface;
    measuring and calculating an xDNA for the estimated color of the surface;

comparing the calculated xDNA for the surface based on the measured reflected light with an observed xDNA for the estimated color of the surface;

determining at least one of an alternate process classification, an alternate material characteristic and an alternate formulation classification to minimize a difference between the observed xDNA for the estimated color of the surface and the calculated xDNA for the surface based on the measured reflected light; and repeating the rendering, measuring and calculating, comparing, and determining steps as necessary to minimize the difference between the observed xDNA for the estimated color of the surface and the calculated xDNA for the surface based on the measured reflected light.

7. A method of processing measured color appearance into a formulation package, comprising:

measuring and calculating, using a computer, an xDNA of a surface being rendered, wherein the xDNA defines a weighted directional response of the surface that includes a set of vectors, and wherein each vector of the set of vectors represents a vector sum of light measured over all of a plurality of reflectance directions at a given wavelength or wavelength range;

accessing, using the computer, a database that includes known or reference process ranges and comparing the xDNA with the known or reference process ranges to determine a process classification;

accessing, using the computer, a database that includes known or reference material characteristics and comparing the xDNA with the known or reference material characteristics to determine a material identification;

accessing, using the computer, a database that includes known or reference materials and comparing the xDNA with the known or reference materials to determine a formulation classification;

using the process classification, material identification and formulation classification to generate a formulation package for the surface being rendered; and implementing the formulation package to render the surface.

8. A method of developing a recipe formulation, comprising:

measuring light reflectance of a surface and calculating, using a computer, an xDNA of the surface based on the measured light reflectance, wherein the xDNA defines a weighted directional response of the surface that includes a set of vectors, and wherein each vector of the set of vectors represents a vector sum of light measured over all of a plurality of reflectance directions at a given wavelength or wavelength range;

accessing, using the computer, a database that includes known or reference material characteristics, comparing the xDNA with the known or reference material characteristic, and using the comparison in a recipe formulation engine;

accessing, using the computer, a database that includes known or reference material characteristics, comparing the xDNA with the known or reference material characteristics, and using the comparison in a process fluid dynamic engine; and generating and implementing, using the computer, a recipe formulation from results of the recipe formulation engine and the process fluid dynamic engine.

9. A method for effectuating a visualization model, comprising:

measuring and calculating, using a computer, an xDNA of a surface, wherein the xDNA defines a weighted directional response of the surface that includes a set of vectors, and wherein each vector of the set of vectors represents a vector sum of light measured over all of a plurality of reflectance directions at a given wavelength or wavelength range;

accessing using the computer a database that includes known or reference material characteristics, comparing the xDNA with the known or reference material characteristics, and using the comparison in a recipe formulation engine;

accessing, using the computer, a database that includes known or reference material characteristics, comparing the xDNA with the known or reference material characteristics, and using the comparison in a process fluid dynamic engine; and generating and implementing, using the computer, a visualization material model from results of the recipe formulation engine and the process fluid dynamic engine.

* * * * *